(12) United States Patent
Tuschl et al.

(10) Patent No.: US 9,169,507 B2
(45) Date of Patent: Oct. 27, 2015

(54) MODIFIED RNA LIGASE FOR EFFICIENT 3' MODIFICATION OF RNA

(71) Applicant: The Rockefeller University, New York, NY (US)

(72) Inventors: Thomas Tuschl, New York, NY (US); Janos Ludwig, New York, NY (US); Yi Pei, New York, NY (US); Carolina Lin, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 14/326,016

(22) Filed: Jul. 8, 2014

(65) Prior Publication Data

US 2015/0010950 A1 Jan. 8, 2015

Related U.S. Application Data

(62) Division of application No. 13/750,522, filed on Jan. 25, 2013, now Pat. No. 8,809,022, which is a division of application No. 12/525,176, filed as application No. PCT/US2008/001227 on Jan. 30, 2008, now Pat. No. 8,383,370.

(60) Provisional application No. 60/887,288, filed on Jan. 30, 2007.

(51) Int. Cl.
*C12P 19/34* (2006.01)
*C12N 9/00* (2006.01)
*C12N 1/20* (2006.01)
*C12N 15/00* (2006.01)

(52) U.S. Cl.
CPC .. *C12P 19/34* (2013.01); *C12N 9/93* (2013.01)

(58) Field of Classification Search
None
See application file for complete search history.

(56) References Cited

PUBLICATIONS

Ho et al., "Bacteriophase T4 RNA Ligase (gp24.1) Exemplifies a Family of RNA Ligases Found in All Phylogenetic Domains", PNAS, vol. 99, No. 20, 12709-12714 (2002).
Yin et al., "Structure-Function Analysis of T4 RNA Ligase 2*", The Journal of Biological Chemistry, vol. 278, No. 20, 17601-17608 (2003).
Kuhne et al., "Continuous In Vitro Evolution of Ribozymes that Operate Under Conditions of Extreme PH", J. Mol. Evol. 57:292-298 (2003).
Ho et al., "Structure and Mechanism of RNA Ligase", Structure, vol. 12, 327-339 (2004).
Nandakumar et al., "RNA Ligase Structures Reveal the Basis for RNA Specificity and Conformational Changes that Drive Ligation Forward", Cell 127, 71-84 (2006).
Chica et al., Curr Opin Biotechnol., Aug. 2005;16(4):378-84.
Sen et al., Appl Biochem Biotechnol. Dec. 2007; 143(3):212-23.

*Primary Examiner* — Christian Fronda
(74) *Attorney, Agent, or Firm* — Hoffmann & Baron, LLP

(57) ABSTRACT

The invention provides a novel truncated mutated T4 RNA ligase 2. In addition, methods are provided for ligating pre-adenylated donor molecules to the 3' hydroxyl group of RNA in the absence of ATP using the ligase.

24 Claims, 22 Drawing Sheets

US 9,169,507 B2

MODIFIED RNA LIGASE FOR EFFICIENT 3' MODIFICATION OF RNA

CROSS-REFERENCE TO RELATED APPLICATIONS

This application is a divisional of U.S. application Ser. No. 13/750,522 filed on Jan. 25, 2013, now U.S. Pat. No. 8,804,022, which is a divisional of U.S. application Ser. No. 12/525,176, filed on Jul. 30, 2009, now U.S. Pat. No. 8,383,370, which is a U.S. National Phase of International Application No. PCT/US2008/001227, filed Jan. 30, 2008, which claims priority from U.S. Provisional Application No. 60/887,288, filed Jan. 30, 2007, all of which are incorporated herein by reference.

The invention described in this application was made with financial support from the National Institutes of Health, Grant Number P01 GM073047-01. The United States government has certain rights in the invention.

BACKGROUND OF THE INVENTION

RNA ligases are used for 3'-labeling of RNAs (the acceptor) by phosphorylated nucleotide analogs or oligonucleotides (the donor) in the presence of ATP (Aravin, 2005; Pfeffer, 2004). The reaction generally requires ATP because the donor molecule 5' phosphate (p) needs to be adenylated by the RNA ligase. The RNA ligase subsequently positions the acceptor molecule 3' hydroxyl terminus for attack on the adenylated donor phosphate (App) resulting in departure of the adenylate in the form of adenosine phosphate (AMP). The result is the formation of a 3' acceptor/5' donor phosphodiester linkage.

The requirement for ATP in ligation is eliminated if pre-adenylated compounds are provided (England, 1977). Non-nucleotidic pre-adenylated compounds can also be used as donor molecule substrates. Biotin or fluorescent dyes have been ligated to the 3' end of tRNAs in this manner.

Most of the literature and commercial products use conventional T4 RNA ligase 1 (Rnl1), but more recently a second ligase has been described and characterized from phage T4, known as T4 RNA ligase 2 (Rnl2) (Ho and Shuman 2002). T4 Rnl2 is a 334 amino acid residue ligase that, like Rnl1, catalyzes intramolecular and intermolecular RNA strand ligation. In contrast to Rnl1, Rnl2 shows nick-sealing activity in a double-stranded RNA or an RNA-DNA context (Nandakumar et al. 2004). A truncated form of this ligase comprising amino acids 1-249 has been shown to maintain adenylyltransferase and AppRNA ligase activity. Deletion of amino acids 34 or 227 in full-length Rnl2 can inactivate the enzyme (Yin et al., 2003), indicating that N-terminal or C-terminal deletions of the enzyme beyond these points very likely would abolish ligase activity. Conservative mutation of residue K227 to Q rescues the activity of ligating pre-adenylated donor RNAs to acceptor RNAs but compromises the enzymes adenylate transfer activity. Some other residues, such as D120, K209, and K225 when mutated also differentially affect ligation of the pre-adenylated donor versus adenylate transfer activity (Yin et al., 2003).

Rnl2(1-249) has, due to its missing C-terminal domain, a reduced affinity for binding phosphate donors and therefore transfers the adenylate residue from the adenylated enzyme to the 5'-phosphate group of miRNA acceptors less efficiently then other ligases. Therefore, Rnl2(1-249) allows consistently better labeling results than Rnl1. Nevertheless, the ratio of desired ligation versus unwanted side reactions, such as circularization and dimerization, still depends on the kinetic parameters of individual steps of the ligase mechanism.

Circularization is a consequence of deadenylation of pre-adenylated donors followed by adenylate transfer to miRNA 5' phosphates forming App-miRNA that will then circularize by attack of the miRNA 3' hydroxyl and also dimerize to a certain degree.

Circularization can be partially suppressed by the use of high concentration donors or reduction of temperature but in cannot be avoided completely. These side reactions are mostly unpredictable and caused by sequence-dependent secondary structure variation of donor and acceptor molecules.

miRNAs are 21- to 23-nt RNA molecules that act as natural regulators of gene expression in plants and animals. In humans about 400 miRNA genes have been identified, and methods to characterize their tissue or cell-type specific expression patterns and their deregulation in disease are needed (Aravin, 2005). MiRNAs are naturally 5' phosphorylated and carry 2',3' dihydroxyl termini.

One of the approaches for detecting miRNAs is based on microarray hybridization that requires fluorescent labeling of the miRNA sample. An RNA ligase is used to conjugate a fluorescently labeled donor to the miRNA. However, the current methods of ligation are plagued by the unwanted side reactions described above.

Accordingly, a need exists for an improved RNA ligase enzyme that can more efficiently modify the 3' position of RNA.

SUMMARY OF THE INVENTION

In a first aspect of the invention an enzyme is provided. The enzyme includes a truncated T4 RNA ligase 2 lacking a C-terminal segment starting with amino acid residue 228 or any higher amino acid residue, and optionally lacking an N-terminal segment starting before amino acid residue 34 or any lower amino acid residue, wherein said enzyme includes a substitution at a location selected from the group consisting of lysine at position 225, lysine at position 227, arginine at position 55, or a combination thereof, with a naturally occurring amino acid, and wherein the truncated T4 RNA ligase is capable of modifying a 3' hydroxyl group of RNA.

In another aspect of the invention, a method is provided for enzymatically ligating a pre-adenylated donor molecule to RNA. The method includes reacting the pre-adenylated donor molecule and the 3' hydroxyl group of a 5' phosphorylated or de-phosphorylated RNA in the absence of adenosine triphosphate and in the presence of an enzyme comprising a truncated T4 RNA ligase 2 lacking a C-terminal segment starting with amino acid residue 228 or any higher amino acid residue, and optionally lacking an N terminal segment before amino acid residue 34 or any lower amino acid residue, wherein said enzyme includes a substitution at a location selected from the group consisting of lysine at position 225, lysine at position 227, arginine at position 55, or a combination thereof, with a naturally occurring amino acid, and wherein the truncated T4 RNA ligase 2 is capable of ligating the pre-adenylated donor molecule to the 3' hydroxyl group of the optionally de-phosphorylated RNA in the absence of adenosine triphosphate.

In another aspect of the invention, a method is provided for enzymatically ligating a pre-adenylated donor molecule to de-phosphorylated RNA. The method includes reacting the pre-adenylated donor molecule with the 3' hydroxyl group of the RNA in the absence of adenosine triphosphate, and in the presence of an enzyme comprising a truncated T4 RNA ligase 2 lacking a C-terminal segment starting with amino acid residue 228 or any higher amino acid residue, and optionally lacking an N terminal segment before amino acid residue 34 or any lower amino acid residue, wherein when both the donor molecule and/or the acceptor molecule are each adenylated at the 5' position and have a free hydroxyl group at the 3' position, the molecule has fewer than sixteen nucleotide residues; and wherein the truncated T4 RNA ligase 2 is capable of ligating the pre-adenylated donor molecule to the 3' hydroxyl group of the de-phosphorylated RNA in the absence of adenosine triphosphate.

In another aspect of the invention, a nucleic acid molecule is provided that encodes an enzyme that includes a truncated T4 RNA ligase 2 lacking a C-terminal segment starting with amino acid residue 228 or any higher amino acid residue, and optionally lacking an N-terminal segment starting before amino acid residue 34 or any lower amino acid residue, wherein said enzyme includes a substitution at a location selected from the group consisting of lysine at amino acid position 225, lysine at amino acid position 227, arginine at amino acid position 55, or a combination thereof, with a naturally occurring amino acid, and wherein the truncated T4 RNA ligase is capable of modifying a 3' hydroxyl group of RNA.

In another aspect of the invention, a kit is provided. The kit includes an enzyme and a donor molecule. The enzyme includes a truncated T4 RNA ligase 2 lacking a C-terminal segment starting with amino acid residue 228 or any higher amino acid residue, and optionally lacking an N-terminal segment starting before amino acid residue 34 or any lower amino acid residue, wherein said enzyme includes a substitution at a location selected from the group consisting of lysine at position 225, lysine at position 227, arginine at position 55, or a combination thereof, with a naturally occurring amino acid, and wherein the truncated T4 RNA ligase is capable of modifying a 3' hydroxyl group of RNA. The donor molecule has formula (1):

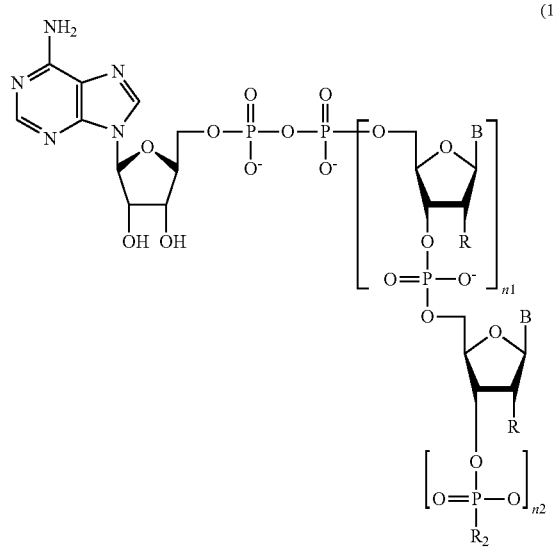

(1)

wherein,
n1=0-25;
R represents H, OH, OCH$_3$, O(CH$_2$)$_2$OCH$_3$, F, NH$_2$; B represents a natural nucleic acid base or base analog, and
when n2=0, R$_2$ represents H, NH$_2$, NHQ, —(CH$_2$)$_n$NH$_2$, or an aminoalkyl linker having a formula —(CH$_2$)$_n$NHQ, —O(CH$_2$)$_n$NH$_2$, —O(CH$_2$)$_n$NHQ, wherein n=2 to 18;

wherein the alkyl chains represented as (CH$_2$)$_n$ are optionally substituted with one or more hydroxymethyl groups; and wherein Q represents an active moiety; and
when n2=1, R$_2$ represents an aminoalkyl linker having a formula —O(CH$_2$)$_n$NH$_2$ or —O(CH$_2$)$_n$—NHQ, wherein n=2 to 18; wherein the alkyl chains represented as (CH$_2$)$_n$ are optionally substituted with one or more hydroxymethyl groups; and wherein Q represents an active moiety,
or formula (2):

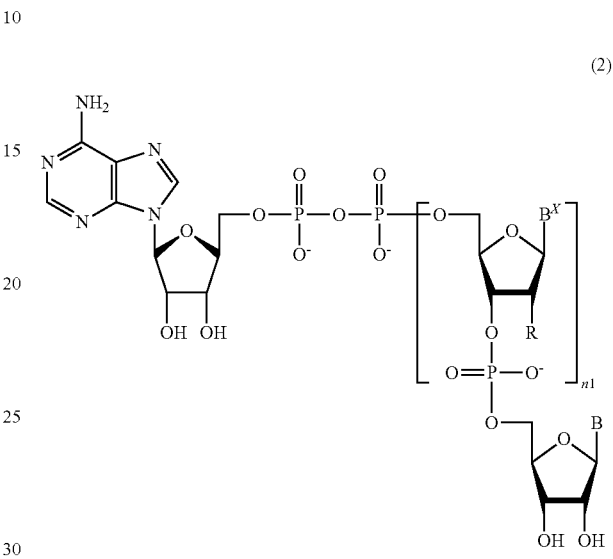

(2)

wherein,
n1=0-25;
R represents H, OH, OCH$_3$, O(CH$_2$)$_2$OCH$_3$, F, NH$_2$;
B represents a natural nucleic acid base or base analog,
X represents —(CH$_2$)$_n$NH$_2$, —(CH$_2$)$_n$NHQ-, —CH=CH—CH—NH$_2$, —CH=CH—CH—NHQ, —CH=CH—C(=O)—NH—(CH$_2$)$_n$NH$_2$, —CH=CH—C(=O)—NH—(CH$_2$)$_n$NH$_2$-Q,
wherein n=2 to 18, or a nucleotide having a pyrimidine base, said nucleotide carrying an aminolinker at a 5-position of the pyrimidine base; and wherein Q represents an active moiety.

DETAILED DESCRIPTION OF THE INVENTION

T4 RNA Ligase

Figure 1:
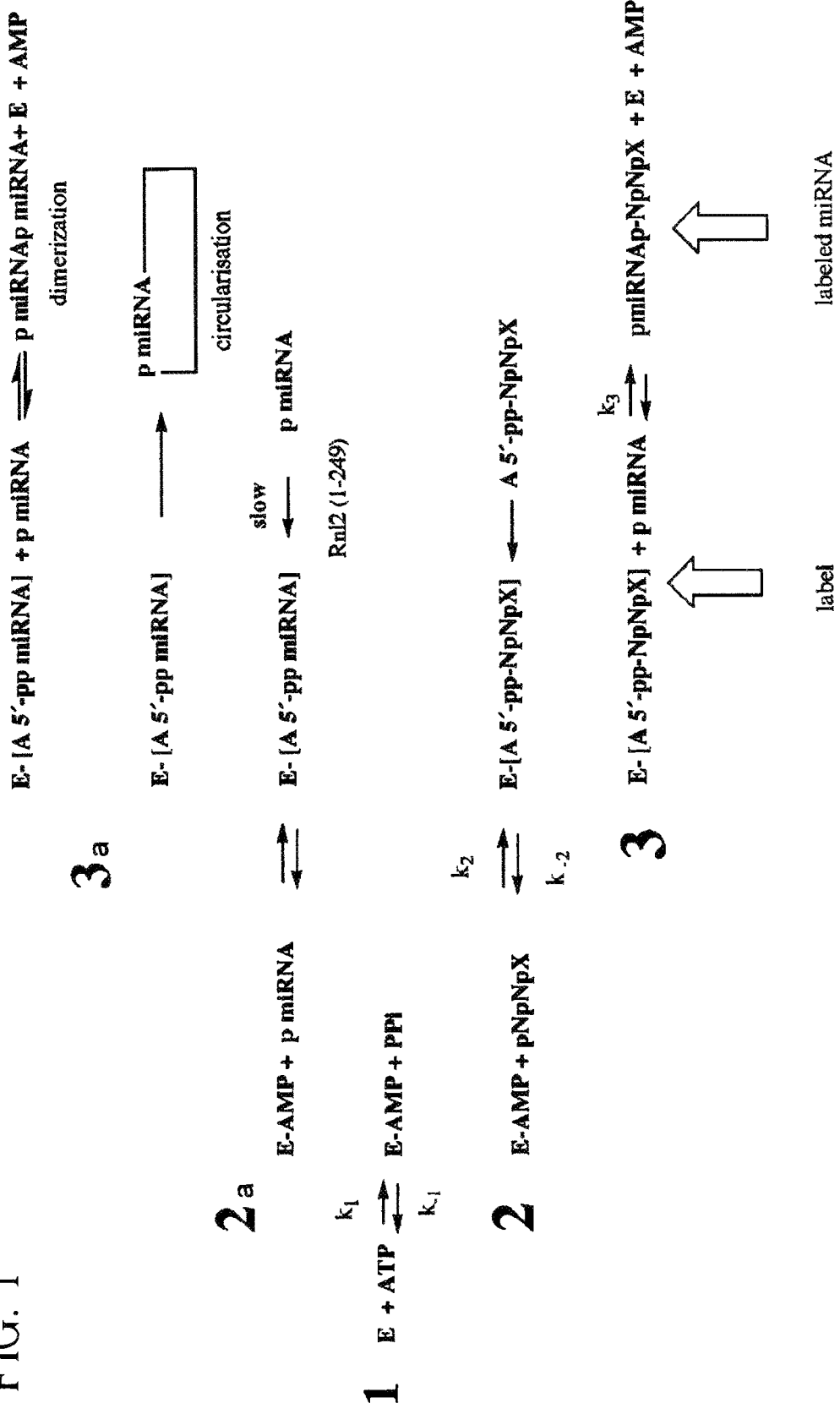
FIG. 1 is a schematic showing the mechanism of RNA ligases.

The present invention provides a novel truncated T4 RNA (Rnl2) ligase enzyme. In order for the enzyme to retain its ligating activity, the truncation should not go beyond amino acid residue 227 at the C-terminal end.

In one embodiment, the truncated Rnl2 ligase lacks the C-terminal segment starting with amino acid residue 228 or any higher amino acid residue, i.e, 228-334. In a preferred embodiment, the ligase lacks the C-terminal segment starting with amino acid 235 or any higher residue, i.e., 235-334. In a more preferred embodiment, the ligase lacks the C-terminal segment starting with amino acid 250 or any higher residue, i.e., 250-334. In a most preferred embodiment, the truncated ligase includes residues 1-249.

The enzyme also optionally lacks the N-terminal segment before amino acid residue 34 or any lower amino acid residue. In another embodiment, the enzyme lacks the N-terminal segment before amino acid 5, or any lower amino acid residue.

It is specifically contemplated that, in the truncations described above, the phrase "C-terminal segment starting with any designated amino acid residue (e.g., 228, 235, or 250) or any higher amino acid residue" means that the truncation of the C-terminal segment may start with the amino acid residue designated or with any amino acid residue between the designated amino acid residue and the last amino acid residue in full length Rnl2 at position 334. For example, in the case where the designated amino acid is 228, the truncation may start at amino acid residue 228, amino acid residue 229, amino acid residue 230, amino acid residue 231, etc. until amino acid residue 334; in the case where the designated amino acid is 235, the truncation may start at amino acid residue 235, amino acid residue 236, amino acid residue 237, amino acid residue 238, etc. until amino acid residue 334; and in the case where the designated amino acid is 250, the truncation may start at amino acid residue 250, amino acid residue 251, amino acid residue 252, amino acid residue 253, etc. until amino acid residue 334.

Similarly, it is specifically contemplated that the phrase "N-terminal segment starting before any designated amino acid residue (e.g., 34 or 5) or any lower amino acid residue" means that the truncation of the N-terminal segment may start at the amino residue immediately preceding the designated amino acid residue or with any amino acid residue between the amino residue immediately preceding the designated amino acid residue and the first amino acid residue in full length Rnl2 at position 1. For example, in the case where the designated amino acid is 34, the truncation may start at amino acid residue 33, amino acid residue 32, amino acid residue 31, amino acid residue 30, etc. until amino acid residue 1; and in the case where the designated amino acid is 4, the truncation may start at amino acid residue 3, amino acid residue 2, or amino acid residue 1.

The enzyme can also be mutated. The mutated enzyme includes a substitution at a location selected from the group consisting of lysine at position 225, lysine at position 227, arginine at position 55, or any combination thereof, with a naturally occurring amino acid. In a preferred embodiment, the lysine at position 225, lysine at position 227, arginine at position 55, or combination thereof is replaced with any of the twenty common naturally occurring amino acid residues that significantly reduce the ability of the enzyme to perform a self adenylation step, as further described below (FIG. 1, step 2, k-2).

In a preferred embodiment, the enzyme includes at least the substitution for the lysine at the 227 position. In this preferred embodiment, the substitution at the 227 position can exist by itself, or with either or both of the substitutions at locations 225 and 55.

Some substitutions are more appropriate than others. For example, conservative replacements of lysine are preferred for the substitution of lysine at the 225 and/or 227 position. For example, gluatimine, asparagine, threonine and serine are each preferred amino acid residues for the substitution because they have similar H-bond interaction potential as, and a somewhat smaller size than, lysine. These substitution residues fit in the 225 and/or 227 positions with relatively little disruption of the enzyme structure. Glutamine is a preferred substitution residue at the 227 position. Other amino acid residues, for example arginine, are preferably used for substituting the lysine residue at position 225. Lysine is the preferred substitution for the arginine located at position 55.

Some amino acid residues are less appropriate to use for substitution. For example arginine is a less appropriate candidate and preferably not used for substituting the lysine residue at position 227.

The truncated and mutated enzyme of the invention is capable of ligating a pre-adenylated donor molecule, as further described below, with the 3' hydroxyl group of an RNA molecule more efficiently and with fewer side reactions, such as circularization and dimerization, than by means currently used.

The methods of the present invention are useful for modifying any type of RNA molecule. Some examples of RNA molecules include those that encode a gene, transfer RNA, messenger RNA, siRNA, and microRNA (miRNA). The RNA may be 5'-phosphorylated or optionally de-phosphorylated.

The enzymes of the present invention may be prepared by methods that are well known in the art. For example, the enzymes of the invention may be made synthetically, i.e. from individual amino acids, or semi-synthetically, i.e. from oligopeptide units or a combination of oligopeptide units and individual amino acids. Suitable methods for synthesizing proteins are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997).

The enzymes may also be made by isolating or synthesizing DNA encoding the enzymes, and producing the recombinant protein by expressing the DNA, optionally in a recombinant vector, in a suitable host cell.

Nucleic acids encoding the enzymes of the invention may be synthesized in vitro. Suitable methods for synthesizing DNA are described by Caruthers et al. 1985. Science 230: 281-285 and DNA Structure, Part A: Synthesis and Physical Analysis of DNA, Lilley, D. M. J. and Dahlberg, J. E. (Eds.), Methods Enzymol., 211, Academic Press, Inc., New York (1992).

Nucleic acid molecules encoding the enzymes of the invention may be designed or assembled from known nucleic acid sequences encoding wild type Rnl2 enzymes. An example of a full-length Rnl2 sequence is provided as NCBI Reference Sequence NP_049790, which is incorporated herein by reference, and is provided in SEQ ID NO: 1. Naturally rimmers, enzymatically active alleles of this sequence are known. The enzyme of the invention, as defined herein, also includes homologues of the enzyme having an amino acid sequence that differs from SEQ ID NO: 1, but that permits the enzyme to retain its ligase activity. For example, a cysteine residue I may replace the glycine (G) residue that appears at position 112 of SEQ ID NO. 1. The amino acid difference does not have known influences on the function of Rnl2 The sequences of Rnl2 enzymes useful in the present invention include, for example: (i) SEQ ID NO. 1; (ii) SEQ ID NO. 1 wherein a cysteine residue I may replace the glycine (G) residue at position 112; (iii) an enzyme that has Rnl2 ligase activity and a sequence that is at least about 95% identical, more preferably at least about 98% identical, and most preferably at least about 99% identical to SEQ ID NO. 1; and (iv) an enzyme that has Rnl2 ligase activity and is a naturally rimmers allele of SEQ ID NO. 1 with a sequence that is at least about 90% identical, more preferably at least about 95% identical, most preferably at least about 98% identical, and optimally at least about 99% identical.

As used herein, the term "sequence identity" means nucleic acid or amino acid sequence identity in two or more aligned sequences, when aligned using a sequence alignment program. The term "% homology" is used interchangeably herein with the term "% identity" herein and refers to the level of nucleic acid or amino acid sequence identity between two or more aligned sequences, when aligned using a sequence alignment program. For example, as used herein, 90% homology means the same thing as 90% sequence identity determined by a defined algorithm, and accordingly a homologue of a given sequence has at least 90% sequence identity over a length of the given sequence.

Optimal alignment of sequences for comparison can be conducted, e.g., by the local homology algorithm of Smith & Waterman, Adv., Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J. Mol. Biol. 215:403-410 (1990), with software that is publicly available through the National Center for Biotechnology Information, or by visual inspection (see generally, Ausubel et al., infra). For purposes of the present invention, optimal alignment of sequences for comparison is most preferably conducted by the local homology algorithm of Smith & Waterman, Adv. Appl. Math. 2:482 (1981). See, also, Altschul, S. F. et al. 1990 and Altschul, S. F. et al., 1997.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondences, as measured using one of the sequence comparison algorithms described herein, e.g. the Smith & Waterman algorithm, or by visual inspection.

A plasmid sequence for the expression of Rnl2(1-249) is provided in SEQ ID NO. 2. Alternatively, the nucleic acid sequence may be derived from a known Rnl2 amino acid sequence using the genetic code, as is routine to those of skill in the art.

The preparation of a truncated Rnl2 (amino acid residues 1-249) is described by Ho et al. (2004), which is incorporated herein by reference. In addition, the mutation of the truncated enzyme can be performed by well known means. For example, the formation, structure and function of various Rnl2 mutants are described in Yin et al. (2003), which is incorporated herein by reference. The mutations in the truncated protein presently claimed can be effected by similar methods.

General methods and procedures for the manipulation of nucleic acids, e.g., polymerase chain reaction (PCR) methods for amplification of nucleic acids, construction of expression vectors, transformation of host cells, and the culture of transformed cells for the production of protein are known. These and many more relevant methods may be found in a variety of laboratory manuals, texts and guides. For a general guide, see, for instance, Sambrook & Russel, (2001) Molecular Cloning, Third edition, Cold Spring Harbor Press. Other useful sources include: Ausubel et al., 1992 Short Protocols in Molecular Biology, Second edition, John Wiley & Son; Gene Expression Technology, Methods in Enzymology Vol. 185 (ed. David Goeddel et al., Academic Press, Inc., London, 1991); Gene Structure and Expression, Second Edition, J. D. Hawkins (Cambridge University Press, London, 1991); PCR Protocols: A Guide to Methods and Applications (Innis, et al. 1990, Academic Press, San Diego, Calif.); Methods in Molecular Biology (Vol. 7), Gene Transfer and Expression Protocols, (ed. E. J. Murray, 1991, The Humana Press Inc., Clifton, N.J.).

A DNA sequence for an expression vector of Rnl2(1-249) 1(227Q is provided in SEQ. ID. NO 3. In the vector, the protein is fused with an N-terminal His tag. The tag is comprised of 10 histines. The start codon for the protein's own first amino acid, Met, starts at position 1074. The ORF ends at position 325 (complementary strand). The start codon for the tag, also a Met, starts at position 1140.

Methods of Enzymatically Ligating

The invention further includes methods of enzymatically ligating a pre-adenylated donor molecule to the 3' hydroxyl group of RNA in the absence of adenosine triphosphate (ATP). In one embodiment, the ligation is conducted in the presence of any of the truncated Rnl2 enzymes that are substituted at positions 225 and/or 227 and/or 55 (mutated enzymes) as described above. It is an advantage of this embodiment that there is no requirement that the RNA is de-phosphorylated. Therefore, the RNA is optionally de-phosphorylated at the 5' location, although it is preferred that the RNA is not de-phosphorylated. The phosphate group of the RNA that is not de-phosphorylated is located at the 5' position and can include any 5' phosphate end, e.g., 5' phosphate, 5' di-phosphate, 5' tri-phosphate, etc.

In another embodiment, the ligation is conducted in the presence of any of the Rnl2 enzymes that are truncated as described above, but that are not substituted at positions 225 and/or 227 and/or 55. In this embodiment, the amino acid residues at positions 225 and 227 are both lysine residues, the residue at position 55 is arginine, and the RNA must be de-phosphorylated. Also in this embodiment, when both the donor molecule and/or the acceptor molecule are adenylated at the 5' position and have a free hydroxyl group at the 3' position, the molecule has fewer than sixteen nucleotide residues, preferably fewer than thirteen nucleotide residues, more preferably fewer than ten nucleotide residues, most preferably fewer than seven nucleotide residues, and optimally fewer than four nucleotide residues.

In both of the above embodiments, the pre-adenylated donor molecule can have formula (1) or formula (2), set forth below.

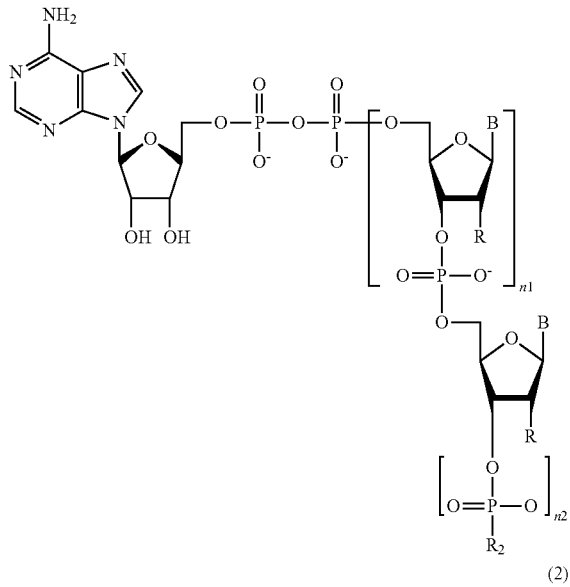

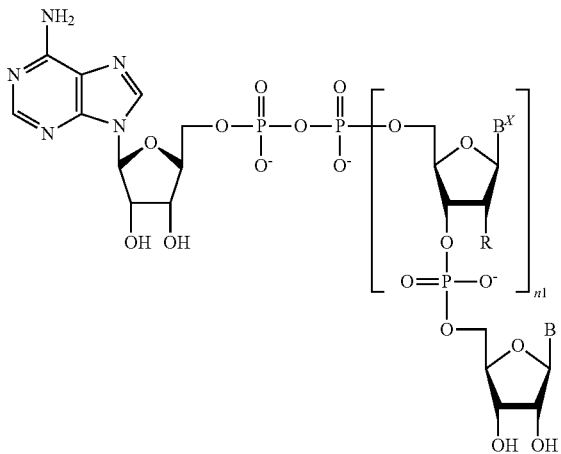

The donor molecule having formula (2) has both a 5' adenyl group and a 3' free hydroxyl group. When the 5' end of the molecule having formula (2) is ligated to the 3' hydroxyl group of an RNA molecule, the ligated product still has a free 3' hydroxyl group. Therefore, the resulting ligated product can react again with a donor molecule having formula (2). With each addition of a molecule having formula (2), the product of the previous reaction increases in length, leading to oligomerization or polymerization. The increase in length can be controlled by means of the time the reaction is permitted to proceed.

In the embodiment wherein the ligation is conducted in the presence of any of the Rnl2 enzymes that are both truncated and mutated as described above, n1 in formula (2) represents 0-25 In the embodiment wherein the ligation is conducted in the presence of any of the Rnl2 enzymes that are truncated as described above, but that are not mutated, n1 in formula (2) represents 0-15.

In both embodiments, R represents H, OH, $OCH_3$, $O(CH_2)_2OCH_3$, F, $NH_2$ and B represents a natural nucleic acid base or base analog in donor molecules having formulas (1) and (2). A natural nucleic acid base is defined herein as any one of the purine or pyrimidine bases commonly found in RNA or DNA, i.e., adenine, guanine, cytosine, thymine or uracil. A base analog is any chemical derivative of the nucleic acids, for example diaminopurine-, which enhances hybridization, or bases with functional group changes, such as 4-thiouridine, for structural studies.

In these donor molecules, when n2=0, $R_2$ represents H, $NH_2$, NHQ, —$(CH_2)_nNH_2$, —$(CH_2)_nNHQ$, —$O(CH_2)_nNH_2$, —$O(CH_2)_nNHQ$, wherein n=2 to 18, preferably 2 to 6, and more preferably 3-6, and wherein Q represents an active moiety. When n2=1, $R_2$ represents an aminoalkyl linker having a formula —$O(CH_2)_nNH_2$ or —$O(CH_2)_nNHQ$, wherein n=2 to 18, preferably 2 to 6, and more preferably 3 to 6, and wherein Q represents an active moiety. The alkyl chains represented as $(CH_2)_n$ are optionally substituted with one or more hydroxymethyl groups. Some examples of $R_2$ with branched hydroxymethyl substituents include —$OCH_2CH$—$(CH_2OH)(CH_2)_4NH_2$ or —$CH_2CH$—$(CH_2OH)(CH_2)_4NHQ$.

In formula (2), X represents —$(CH_2)_nNH_2$, —$(CH_2)_nNHQ_n$, —CH=CH—CH—$NH_2$, —CH=CH—CH—NHQ, —CH=CH—C(=O)—NH—$(CH_2)_nNH_2$, —CH=CH—C(=O)—NH—$(CH_2)_nNH_2$-Q, wherein n=2 to 18, or a nucleotide having a pyrimidine base, said nucleotide carrying an aminolinker at a 5-position of the pyrimidine base; and wherein Q represents an active moiety.

In a preferred embodiment of the donor molecules of formula (1) and formula (2), n1=0-3, R represents H, B represents cytosine, uridine, thymidine, or adenosine, most preferably cytosine; and $R_2$ represents —$OCH_2CH$—$(CH_2OH)(CH_2)_4NH_2$ or —$CH_2CH$—$(CH_2OH)(CH_2)_4NHQ$.

The active moiety Q in formula (1) and formula (2) can be any moiety that performs a useful function, such as assisting in the detection or isolation of the molecule of which the moiety is a part. Examples of moieties assisting in detection include fluorescent labels, enzyme labels, radioisotopes, chemiluminescent labels, electrochemiluminescent labels, and bioluminescent labels, metal particles that can be removed by a magnet, and members of specific molecular binding pairs as described above.

Examples of fluorescent labels which may be used in the invention include 5or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites. In a preferred embodiment, the active moiety is a dye, preferably an organic dye, such as, for example, Cy5, Cy3 or fluorescein.

Examples of enzymatic labels which may be used in the invention include horse radish peroxidase (HRP), alkaline phosphatase (ALP or AP), beta-galactosidase (GAL), glucose-6-phosphate dehydrogenase, beta-N-acetylglucosamimidase, beta-glucuronidase, invertase, xanthine oxidase, firefly luciferase and glucose oxidase (GO).

Examples of luminescent labels which may be used in the invention include luminol, isoluminol, acridinium esters, 1,2-dioxetanes and pyridopyridazines. Examples of electrochemiluminescent labels include ruthenium derivatives.

Examples of radioactive labels which may be used in the invention include radioactive isotopes of iodide, cobalt, selenium, tritium, carbon, sulfur and phosphorous.

In another preferred embodiment, the active moiety is a member of a specific molecular binding pair. A specific molecular binding pair as defined herein is a pair of molecules that specifically bind to each other. Many different types of specific molecular binding pairs are known in the art. Some suitable examples include a cellular receptor and a ligand; an antibody and an antigen; and biotin and avidin or streptavidin. Either member of such pairs are suitable active moieties for the purposes of the present invention. Examples of commonly used specific molecular binding pairs include biotin/avidin, biotin/streptavidin, and digoxigenin/monoclonal anti-digoxigenin antibody. When an antibody is a member of a specific molecular binding pair, the whole antibody, or a fragment that includes the binding domain of the antibody, for example, a single chain antibody, may be used. Preferred members of specific molecular binding pairs include biotin and digoxigenin.

The active molecule can also include rimmers residues, such as cholesterol. Derivatisation with rimmers residues is a successful strategy to enhance in vivo uptake of small interfering RNAs for pharmaceutical applications.

In another embodiment, the donor molecule has formula (3).

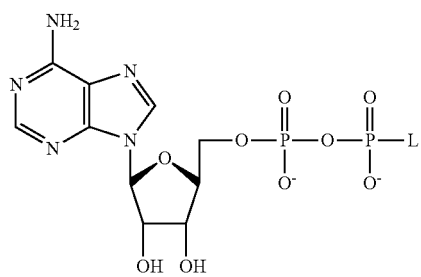

(3)

wherein L represents an aminoalkyl linker having a formula —O(CH$_2$)$_n$—NH$_2$ or —O(CH$_2$)$_n$NHQ, wherein n=2-18, preferably 2-8, more preferably 3-6; wherein the alkyl chains represented as (CH$_2$)$_n$ are optionally substituted with one or more hydroxymethyl groups; and wherein Q represents an active moiety as described above. Donor molecules of formula (3) enable transfer of the L residue as 3'-phosphate ester to the 3'end of RNA with a minimum of structural change.

The temperature at which the ligation takes place can be important. Reduction of temperature of the ligation reaction can positively influence the ligation/circularization ratio. It is preferred that the ligation reaction occur at a maximum temperature of about 25° C., more preferably about 22° C., most preferably about 10° C. Preferably, the ligation reaction occurs at a temperature of about 0° C.

The invention also includes DNA molecules encoding any of the truncated and mutated Rnl2 ligases described above. Further, the invention includes kits comprising any of the truncated and mutated Rnl2 ligases described above as well as any of the donor molecules described above.

Characterization of the Modified RNA Ligase 2 of the Invention that Results in Favorable RNA 3' End Ligation In order to obtain a generally useful, efficient ligase-based labeling or adaptor ligation system, the inventors concluded that a reduction of the rate of the self-adenylation step (k$_{-2}$) might provide a solution (FIG. 1). Thus, if the chemical step of E-AMP formation is slow or 0, this will lead to a reduced levels of E-AMP and limit p-miRNA adenylation and following reactions.

FIG. 1 is a schematic showing the mechanism of RNA ligases. The reaction mechanism involves three distinct steps (lower part of the scheme Steps 1-3). Step 1 is the reaction with ATP to form a covalent lysyl-N AMP intermediate, termed E-AMP. In step 2 the AMP is transferred to the 5'-phosphate end of the donor (pNpNpX) to form an adenylate intermediate, AppNpNpX. In step 3 nucleophilic attack of the acceptor 3'-OH forms the new internucleotide linkage. The scheme marks side reactions from the viewpoint of labeling, i.e. 5'-phosphate activation of 5' phosphorylated miRNA acceptors (pmiRNA) in Steps 2a and 3a. In the absence of ATP, the reverse step 2 is a source of E-AMP, leading to side products (circles and dimers) as shown in Step 3a.

The Rnl2(1-249) ligase mutant cannot perform the reverse step 2 reaction of FIG. 1 at low temperature, while still allowing to the intermolecular ligation step 3 at only slightly a reduced rate.

The mutant was prepared by exchanging lysine (K) residue 227 by glutamine (Q) and the enzyme is thus referred to as Rnl2(1-249)K227Q. K227 is one of two lysines which interact with the adenylate phosphate during the AMP phosphoramidate formation on K35, but it is has no direct phosphate contact in the rearranged active conformation of the enzyme, which forms immediately before the attack of 3'-OH of the acceptor. K35 itself plays multiple roles in this mechanism and cannot be modified without destroying ligation activity.

When the formation of E-AMP is prevented, intermolecular ligation with adenylated donors occurs essentially without side reactions in a clean two-component system. This property of the modified enzyme allows, in principle, the solution for the sequence independent 3' ligation problem, because residual starting material can be converted to products by repeated heating-cooling cycles or sufficiently long reaction times for miRNAs having inaccessible 3' hydroxyl groups.

The mutation was performed in the context of the shortened version of Rnl2 lacking the C-terminal domain, i.e. Rnl2(1-249), because the shortened version is much less sensitive to the presence of E-AMP in terms of the activation of 5'-monophosphates. The level of required reduction of k$_{-2}$ by the mutation is therefore expected to be lower with this enzyme than with the full length version.

The changes caused by the mutation were observed indirectly by measuring the concentration of the circularization and dimerization byproducts formed in the ligation reaction.

Figure 2A:
FIGS. 2A and 2B show a gel electrophoresis of reaction products of miR-16 (FIG. 2A) miR-21 (FIG. 2B) labeled with Rnl2(1-249)K227Q mutant and AppdCpdC-c$_7$-NH$_2$ donor.
Figure 2B:
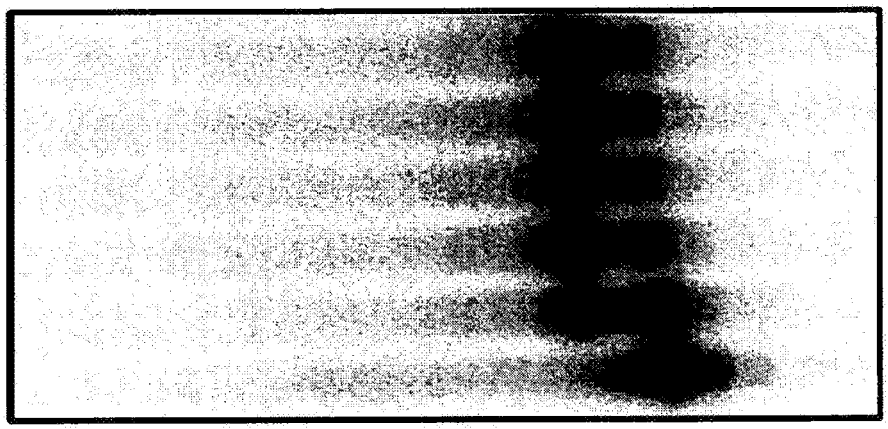
Figure 3A:
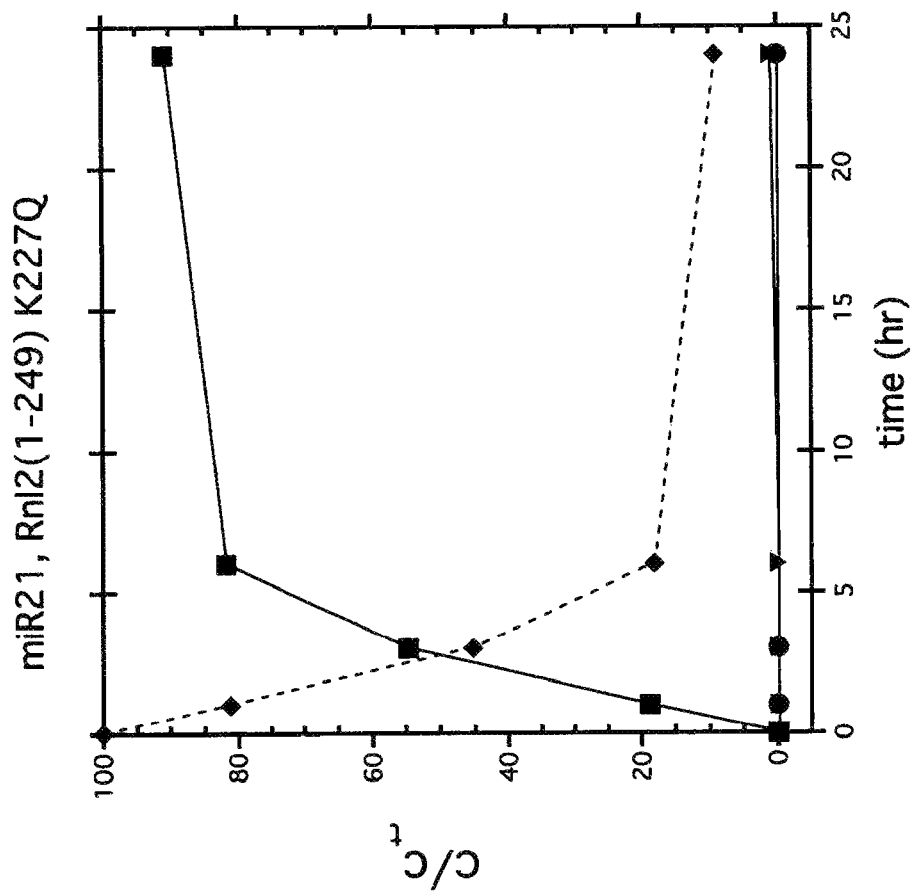
FIGS. 3A-3D are graphs showing the time course of labeling reactions with AppdCpdC-c$_7$-NH$_2$ donor by Rnl2(1-249)K227Q for miR-21 (FIG. 3A), Rnl2 (1-249) for miR-21 (FIG. 3B), Rnl2 (1-249) K227Q for miR-16 (FIG. 3C) and Rnl2 (1-249) for miR-16 (FIG. 3D).
Figure 3B:
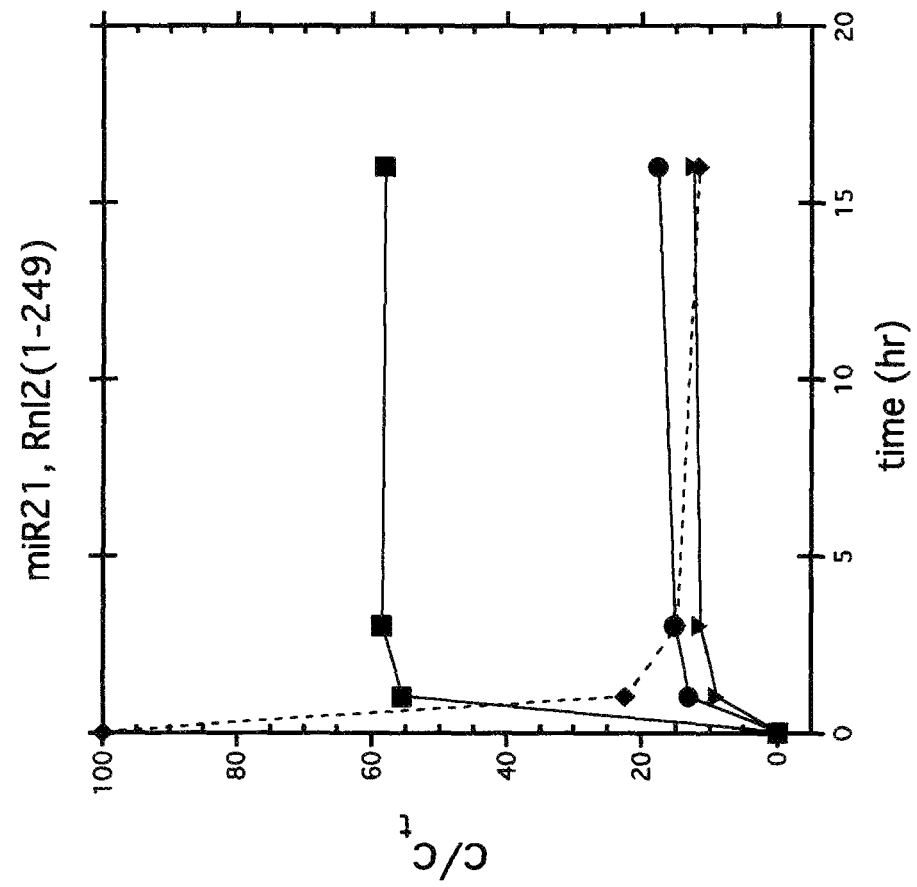
Figure 3C:
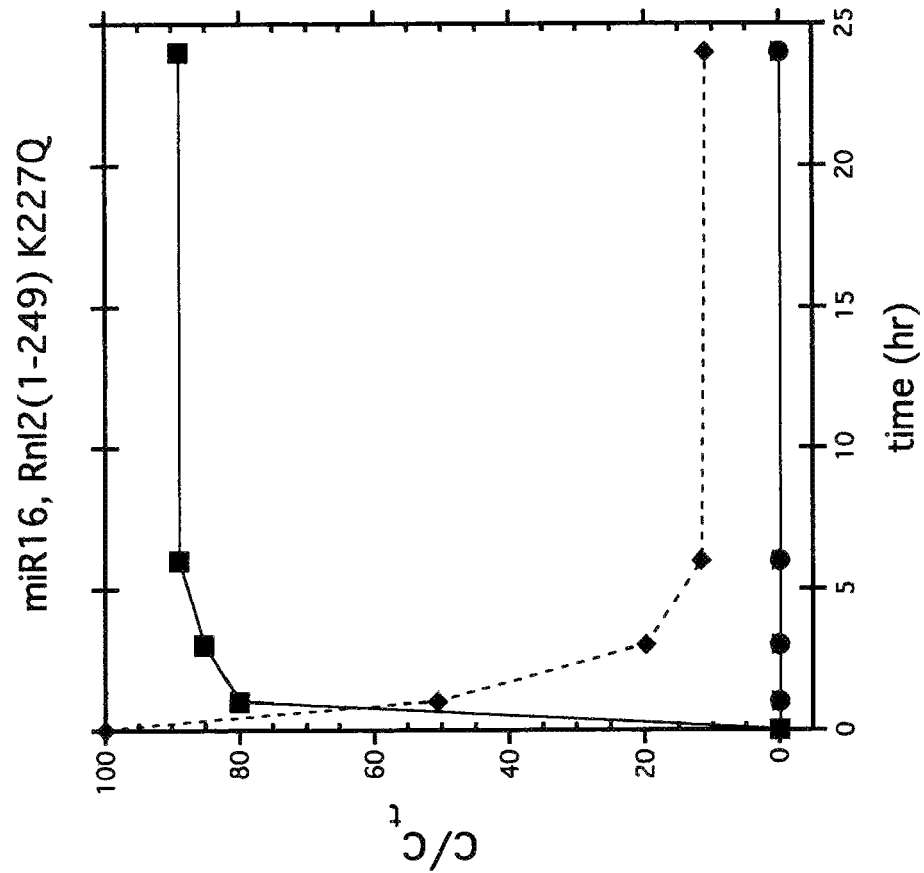
Figure 3D:
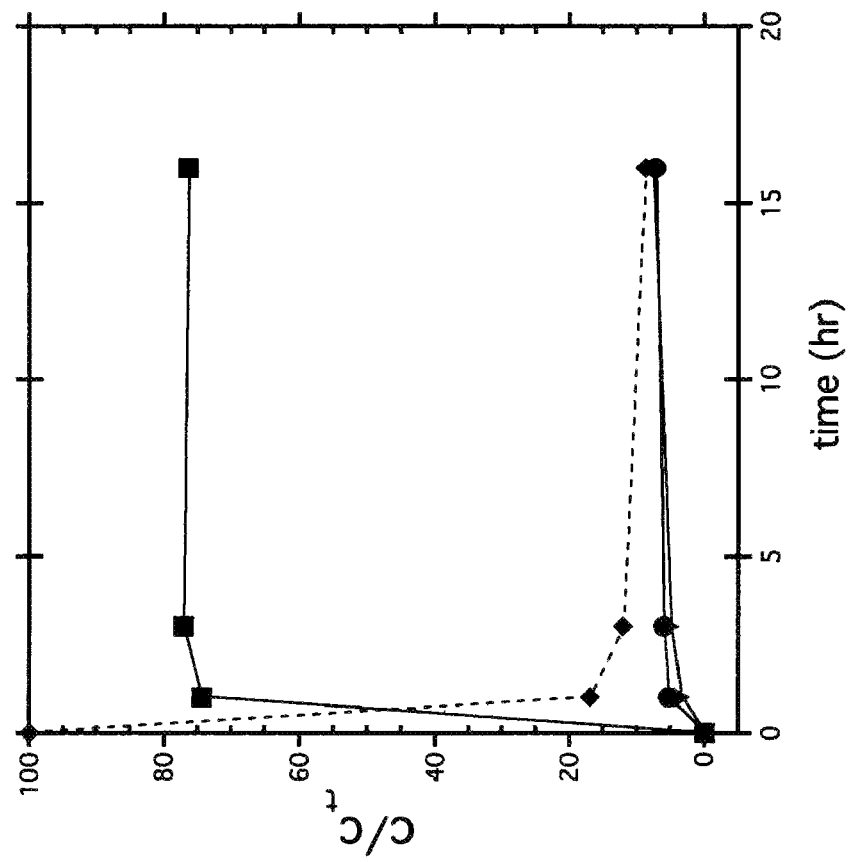

Two model sequences miR-16 and miR-21 were used for comparing the properties of Rnl2(1-249)K227Q and Rnl2(1-249) in the ligation reaction of 5'-phosphorylated acceptor sequences. FIGS. 2A and 2B show a gel electrophoresis of reaction products of miR-16 (FIG. 2A) miR-21 (FIG. 2B) labeled with Rnl2(1-249)K227Q mutant and AppdCpdC-c$_7$-NH$_2$ donor. The miRNA was heated to 90° for 30 sec in the ligation buffer, then rapidly cooled to 0° C. The reaction was started by addition of the enzyme at 0° C. Starting concentration of acceptors miR-21 and miR-16 was 50 Nm, of the donor AppdCpdC-c$_7$-NH$_2$ 10 µM. Enzyme concentration was 1.5 µM. RNA ligation buffer: 50 Mm Tris-HCl, Ph 7.5, 10 Mm MgCl2, 10 Mm beta-mercaptoethanol, 0.1 mg/ml acetylated BSA, 15% DMSO. The reaction was performed at 0° C. Lane 1 contains starting material. Lane 2, 3, 4, 5 contain samples at 1, 3, 6, 24 h reaction time. Lane 6 contains sample at 24 h total incubation time after repeated addition of the enzyme at 6 h. The two arrows in FIG. 2B point to the position of dimer and circular side products, which are side products that are much reduced or eliminated in comparison to the use of the non-mutant ligase.

As shown in FIG. 2A, miR-16 has no stabile secondary structural elements, while FIG. 2B shows miR-21 can form several small hairpin loops. Under optimal conditions at 0° C. the Rnl2(1-249)K227Q mutant performs the ligation without circularization with these model sequences. In FIG. 2B, the upper arrow points to the position of dimerization products and the lower arrow points to the position of circularization products.

FIGS. 3A-3D compare the time course of product formation of the two RNA ligase enzymes. Reaction conditions were as described for FIG. 2. Symbols: ♦ starting material, ■ ligation product, ● circularization product, ▲ dimer. 32P-labeled compounds were quantified using autoradiography. The important new property is that for the mutant enzyme no upper limits in product accumulation can be observed. In the case of the non-mutated enzyme, competitive side reactions set an upper limit for ligation yield, which is 60% with miR-21, and 80% with miR-16. The origin of the slower ligation rate for the mutant is not understood. Without being bound by theory, the origin may be the chemical step or it may reflect a slow structural reorganization of a subpopulation of acceptor sequences, which react on the circularization pathway with Rnl2(1-249). Subsequent addition of the enzyme further increased product formation.

Figures 4A, 4B:
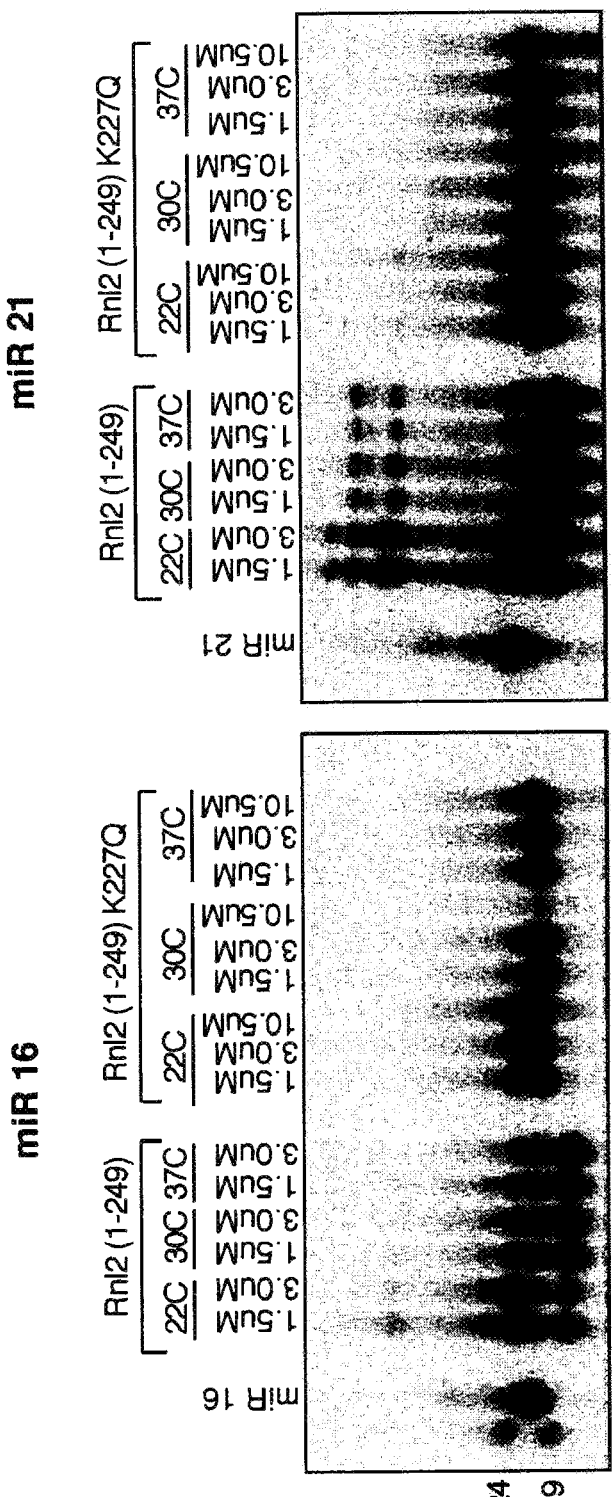
FIGS. 4A and 4B are graphs showing temperature dependence of the ligation reactions in the 22-37° C. range for miR-16 (FIG. 4A) and miR-21 (FIG. 4B).

FIGS. 4A and 4B are graphs showing temperature dependence of the ligation reactions in the 22-37° C. range for miR-16 (FIG. 4A) and miR-21 (FIG. 4B). The miRNA was heated to 90° for 30 s in the ligation buffer, then rapidly cooled to 0° C. The reaction was started by addition of the enzyme at 0° C., followed by bringing the reaction to 22° C., 30° C., or 37° C. for 1 hour. Starting concentration of acceptors miR-16 and miR-21 was 50 Nm, of the donor Appd-CpdC-c$_7$-NH$_2$ 10 µM. Enzyme concentration was varied as 1.5, 3.0, or 10.5 µM. RNA ligation buffer: 50 Mm Tris-HCl, Ph 7.5, 10 Mm MgCl2, 1 Mm DTT, 0.1 mg/ml acetylated BSA, 15% DMSO.

As shown in FIGS. 4A and 4B, the optimal reaction temperature for Rnl2(1-249)K227Q is between 0 and 10° C. Temperatures above 30° C. inactivate the enzyme. FIGS. 4A and 4B also show that the circularization and ligation ratio of Rnl2(1-249) is temperature dependent; ligation is dominant at lower temperatures. The time dependence of ligation product of the mutant follows a similar tendency as the temperature dependency, while the circularization product is missing over the whole range. When using longer reaction times (>10 hr) at these higher reaction temperatures some level of circularization depending on the sequence of the acceptor, still occurred. With the Rnl2(1-249)K227Q, however, no circularization products were detected until 24 hr at 0° C. This is an indication that a specific enzyme donor conformation is required for observing the large reduction in $k_{-2}$. This aspect of the enzyme is different from the rate reduction of self adenylation by ATP which is merely 3.8% with the K227Q mutation in the full length Rnl2

Figure 5A:
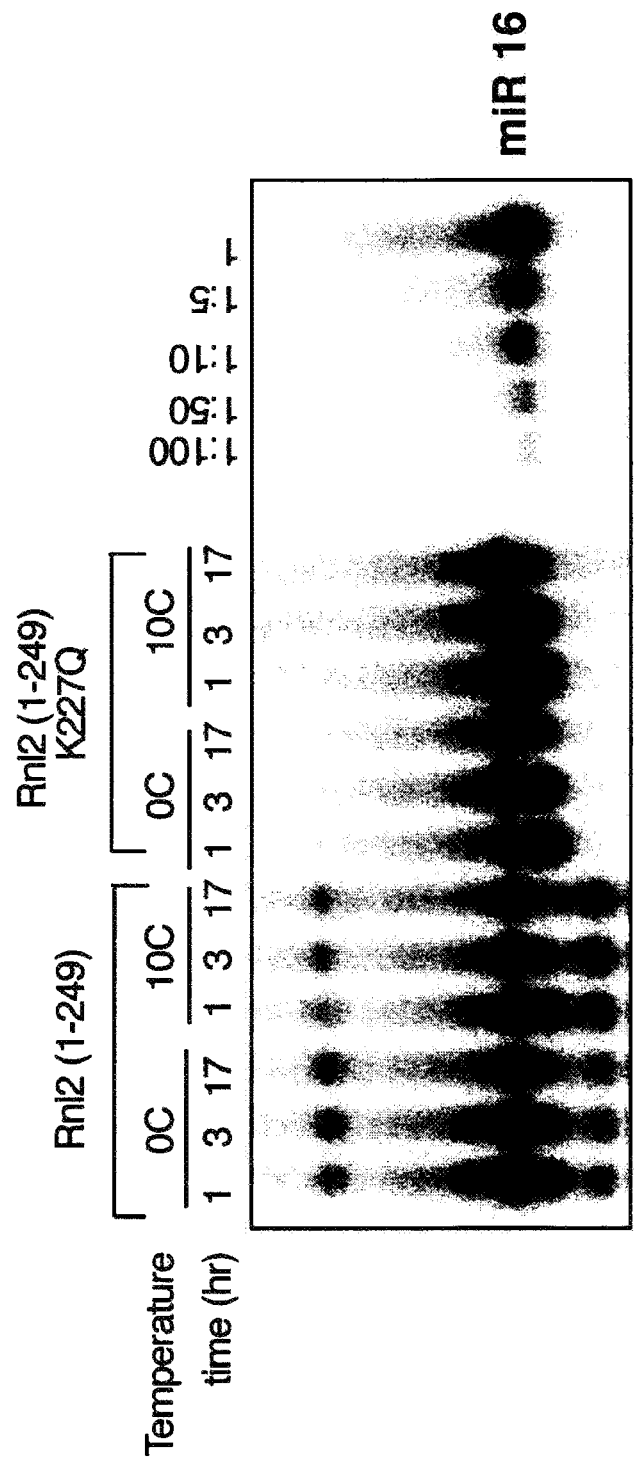
FIGS. 5A and 5B show a gel rimmers resis of reaction products for time course of labeling reaction by Rnl2(1-249) and Rnl2(1-249)K227Q for miR-21 (FIG. 5B) and miR-16 (FIG. 5A) with AppdCpdC-c$_7$-NH$_2$ donor at 0° C. and 10° C.

Time course of the reaction for Rnl2(1-249)K227Q and Rnl2(1-249) with miR-16 and mir-21 is shown in FIGS. 5A and B and 6A-H.

Figure 5B:
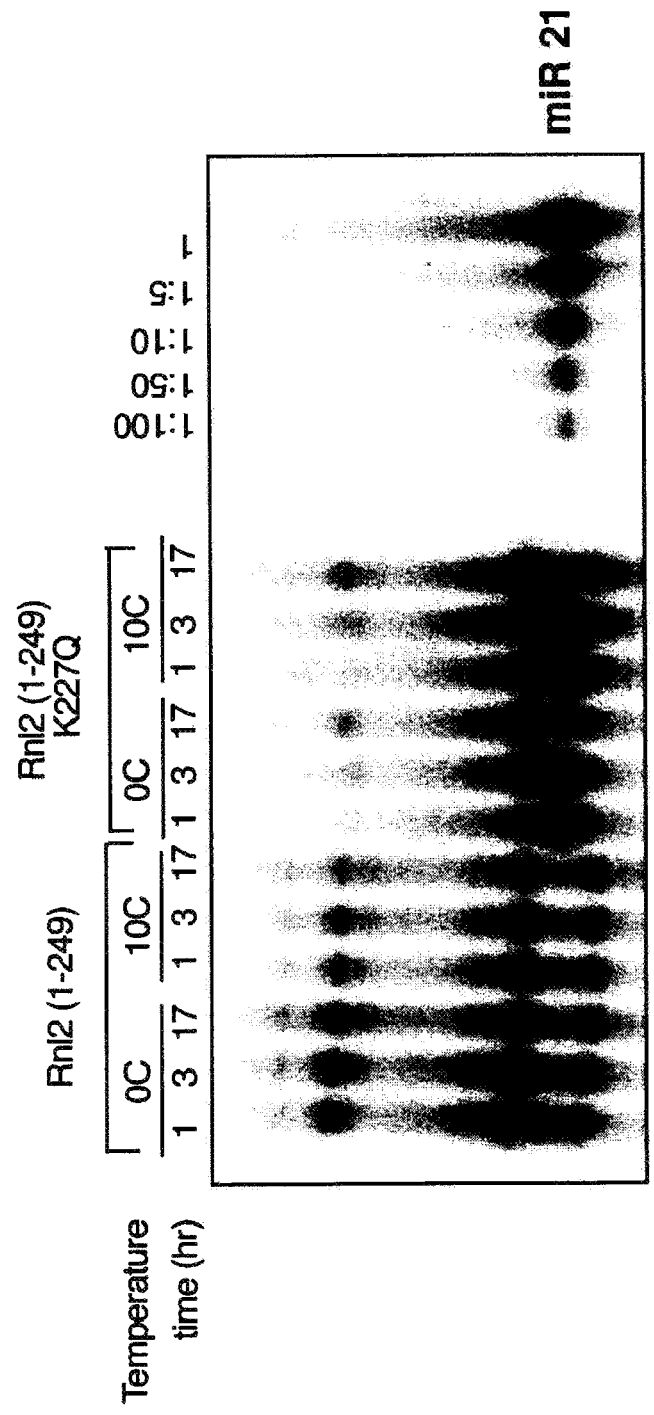
Figure 6A:
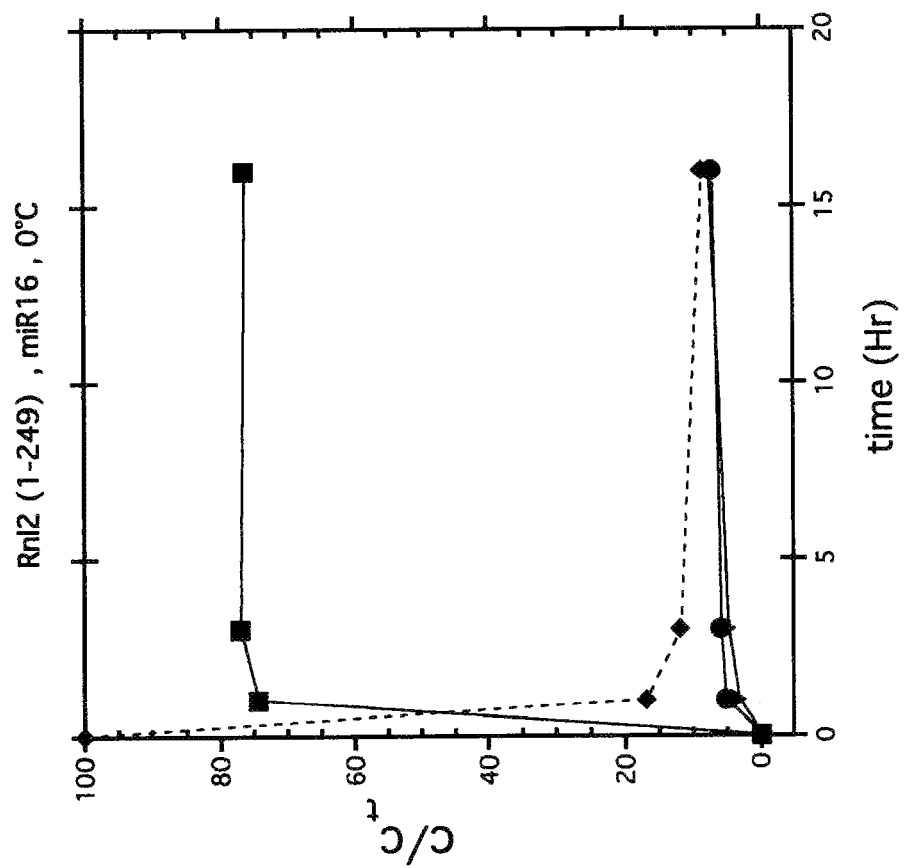
FIGS. 6A-6H are graphs showing a comparison of the time course of labeling reactions by Rnl2(1-249) and Rnl2(1-249) K227Q for miR-16 and miR21 with AppdCpdC-c$_7$-NH$_2$ donor at 0° C. and 10° C.
Figure 6B:
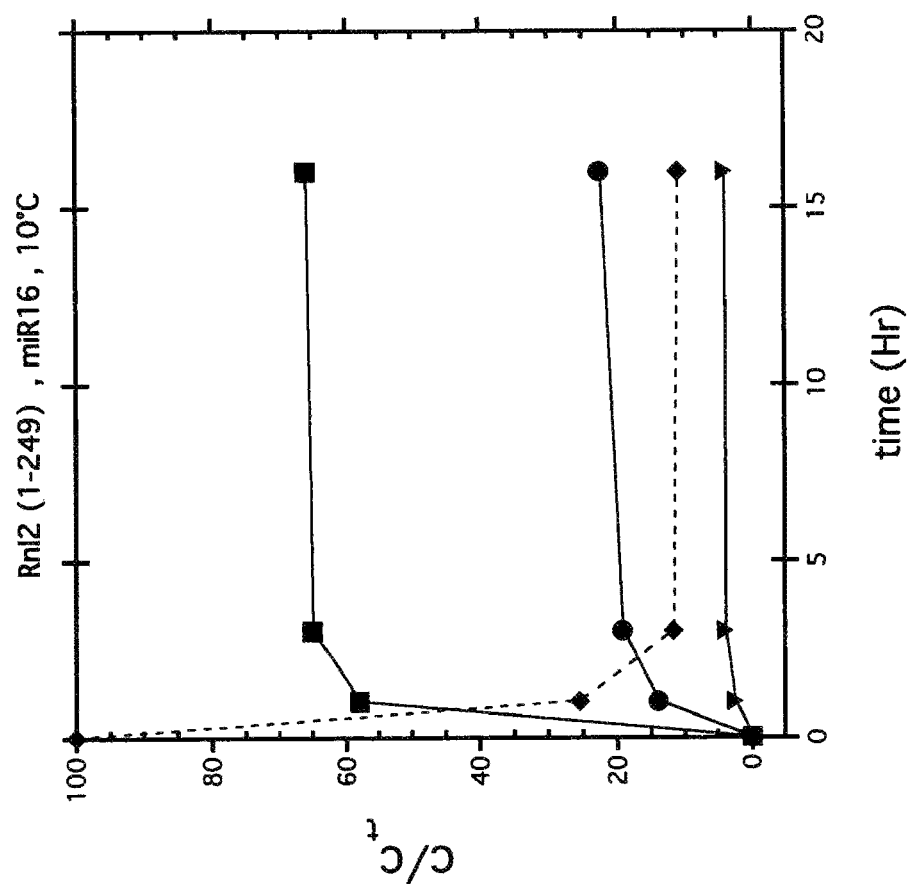
Figure 6C:
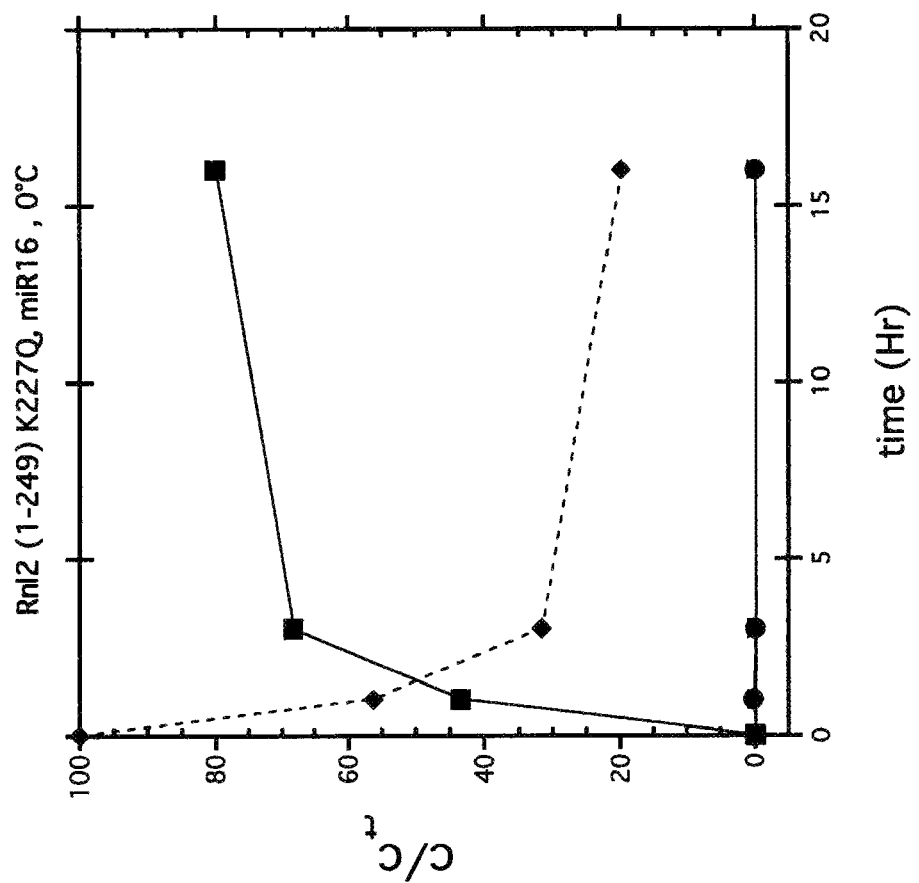
Figure 6D:
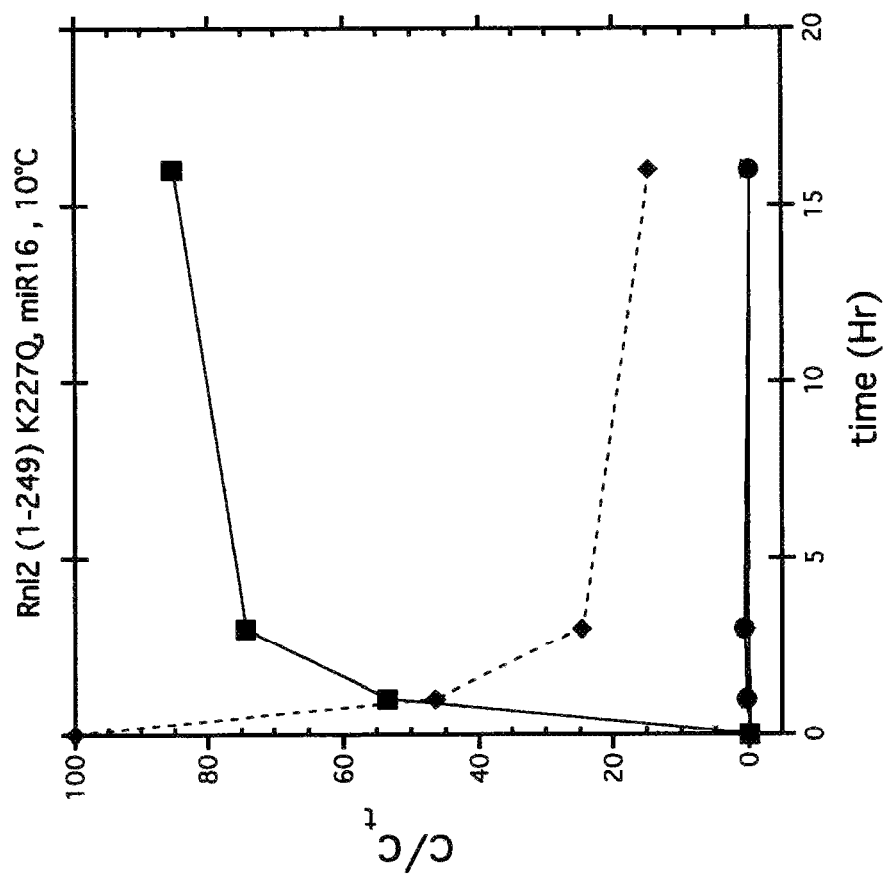
Figure 6E:
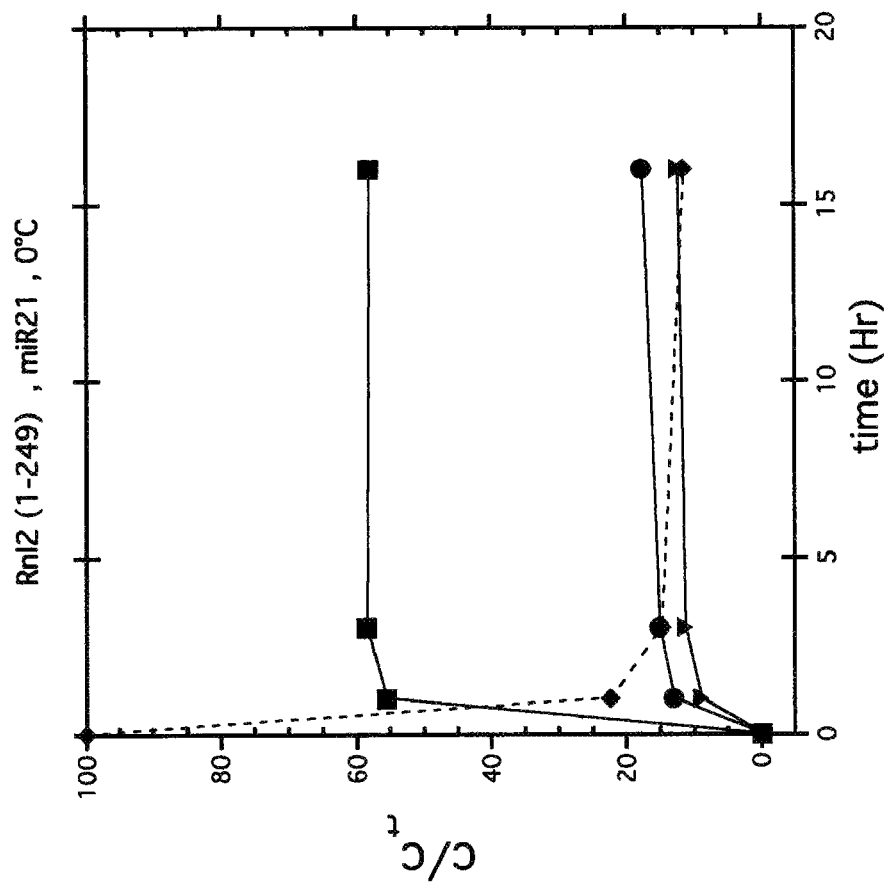
Figure 6F:
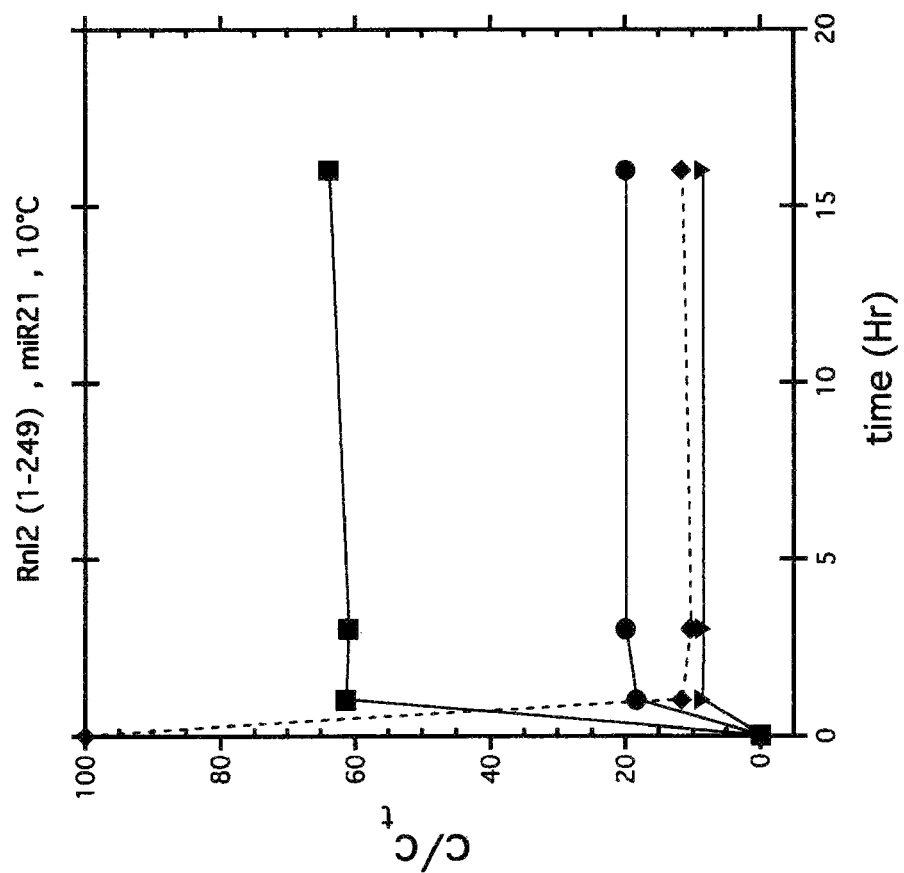
Figure 6G:
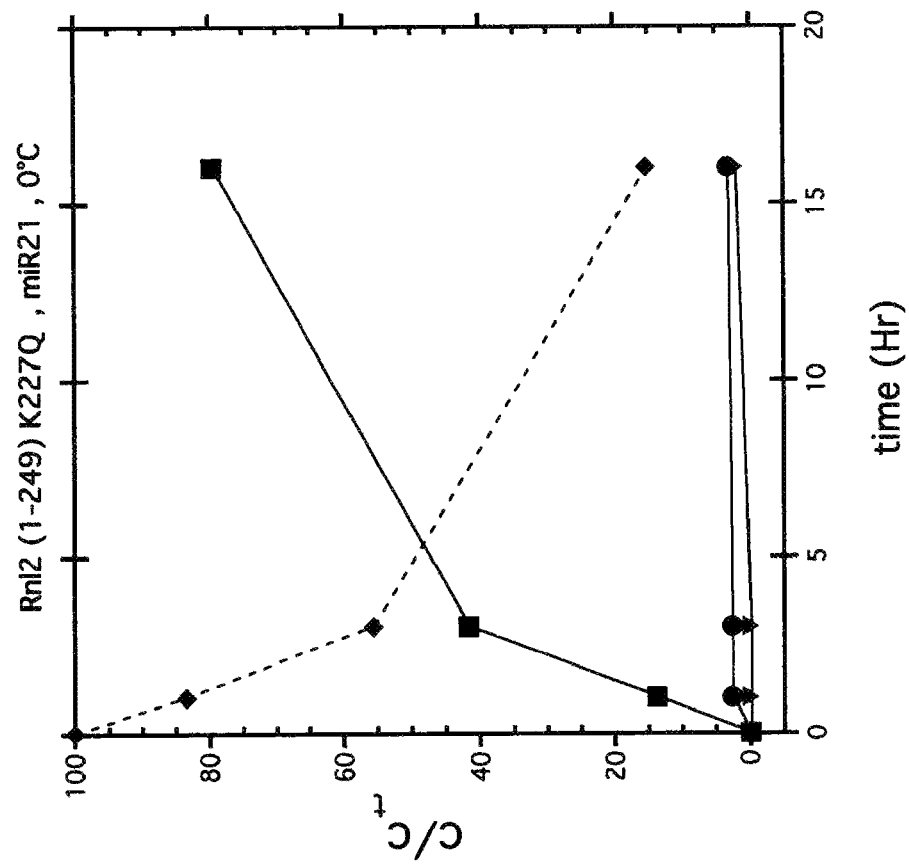
Figure 6H:
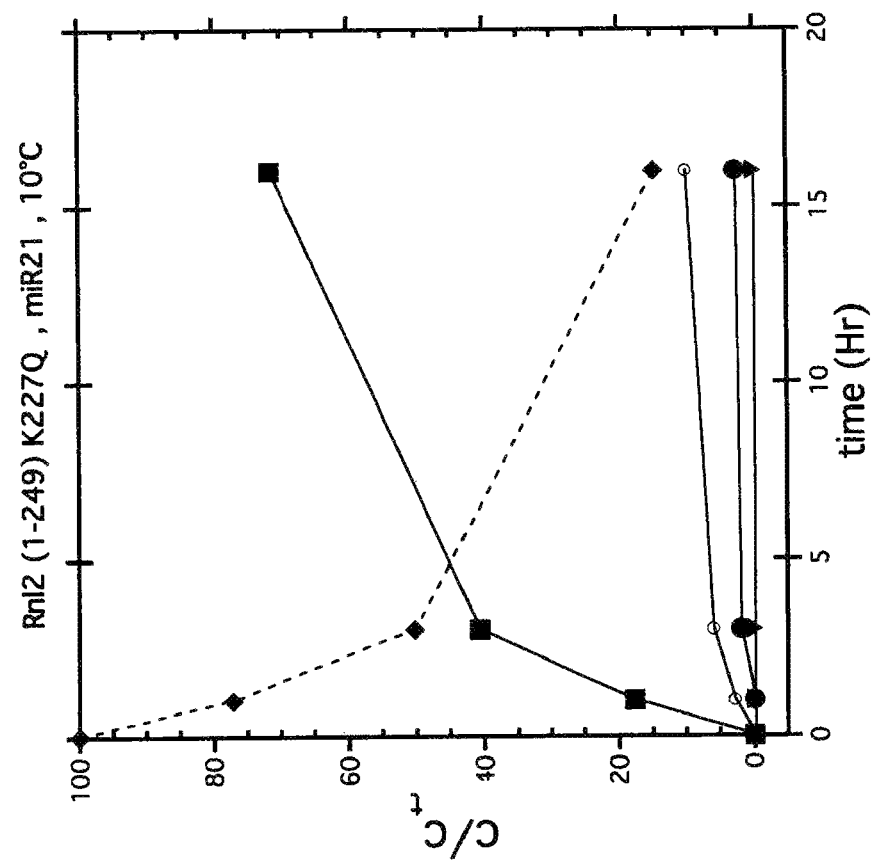

FIGS. 5A and B show a gel rimmers resis of reaction products for time course of labeling reaction by Rnl2(1-249) and Rnl2(1-249)K227Q for miR-21 (FIG. 5B) and miR-16 (FIG. 5A) with AppdCpdC-c$_7$-NH$_2$ donor at 0° C. and 10° C. Reaction conditions were described for FIG. 2, followed by keeping the reactions at 0° C., or bringing it to 10° C., with the Rnl2(1-249) and Rnl2(1-249)K227Q. Time points were taken at 1, 3, and 17 hours. A dilution series of the starting material is presented on the right.

FIGS. 6A-6H are graphs showing a comparison of the time course of labeling reactions by Rnl2(1-249) and Rnl2(1-249) K227Q for miR-16 (FIG. 6A-6D) and miR-21 (FIG. 6E-6H) with AppdCpdC-c$_7$-NH$_2$ donor at 0° C. and 10° C. Reaction conditions were as described for FIG. 2, followed by keeping the reactions at 0° C. or bringing it to 10° C., with the Rnl2 (1-249) and Rnl2(1-249)K227Q. Time points were taken at 1, 3, and 17 hours. Symbols: ♦ starting material, ■ ligation product, ● circularization product, ▲ dimer. 32P-labeled compounds were quantified using autoradiography.

In FIGS. 5A-5B and 6A-6H, the mutant enzyme shows a slower rate of product formation, depending on acceptor sequence. A hypothetical explanation for this effect is that reaction of 3'end and 5'end of the acceptors follow different kinetics, so the slow component of the miR21 ligation results from a structural reorganization around the 3'end. With the wild type enzyme this subpopulation undergoes circularization and the slow component is not observed.

Figure 9:
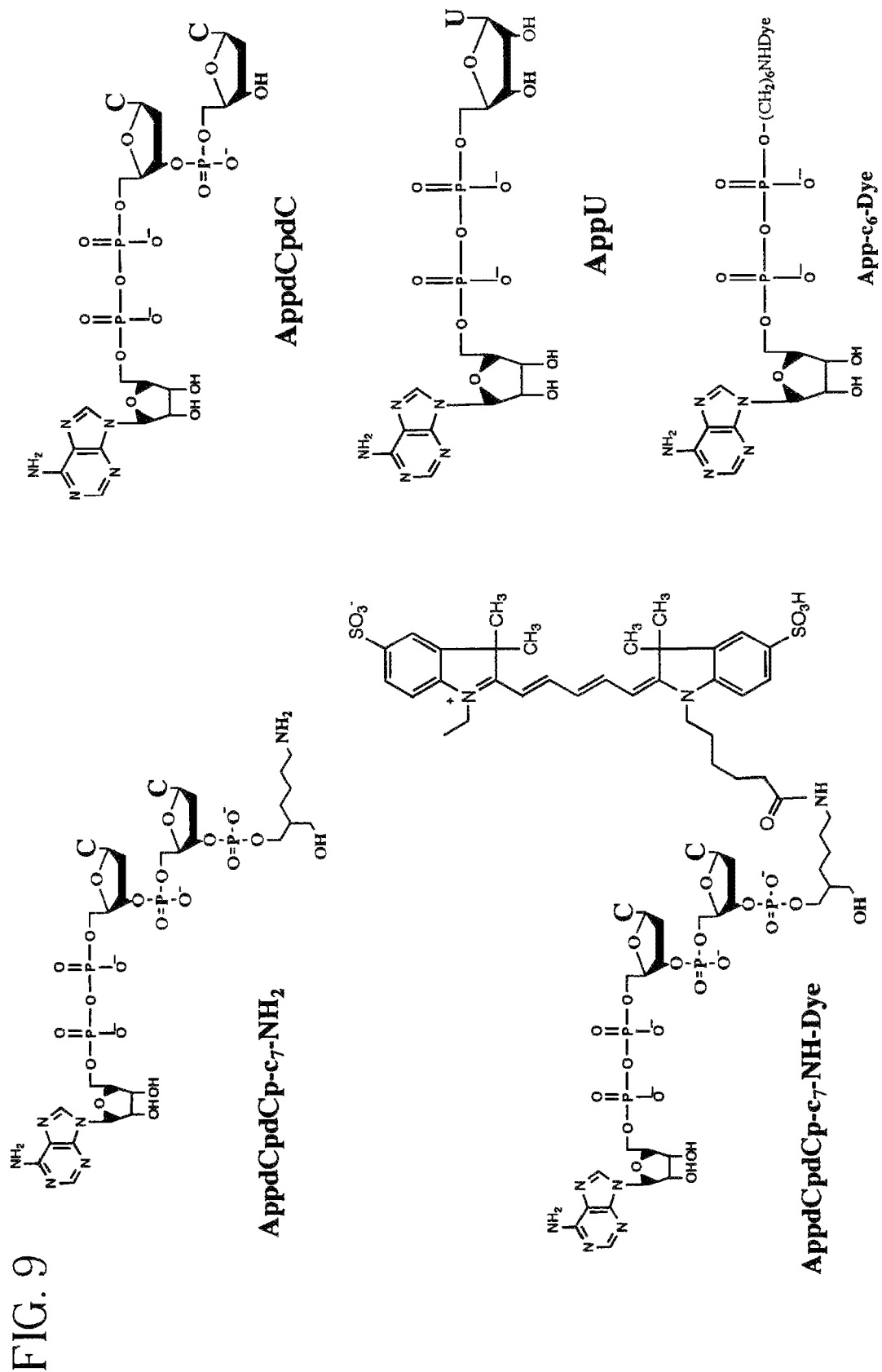
FIG. 9 shows the structure of donors.

Examples of the structure of possible donor molecules for the ligation reaction are presented in FIG. 9. The AppdCpC-c7-NH2 was synthesized on a commercial aminolinker CPG. Attachment of a fluorescent marker to the terminal amino group does not influence the substrate properties of the donor.

Figure 7:
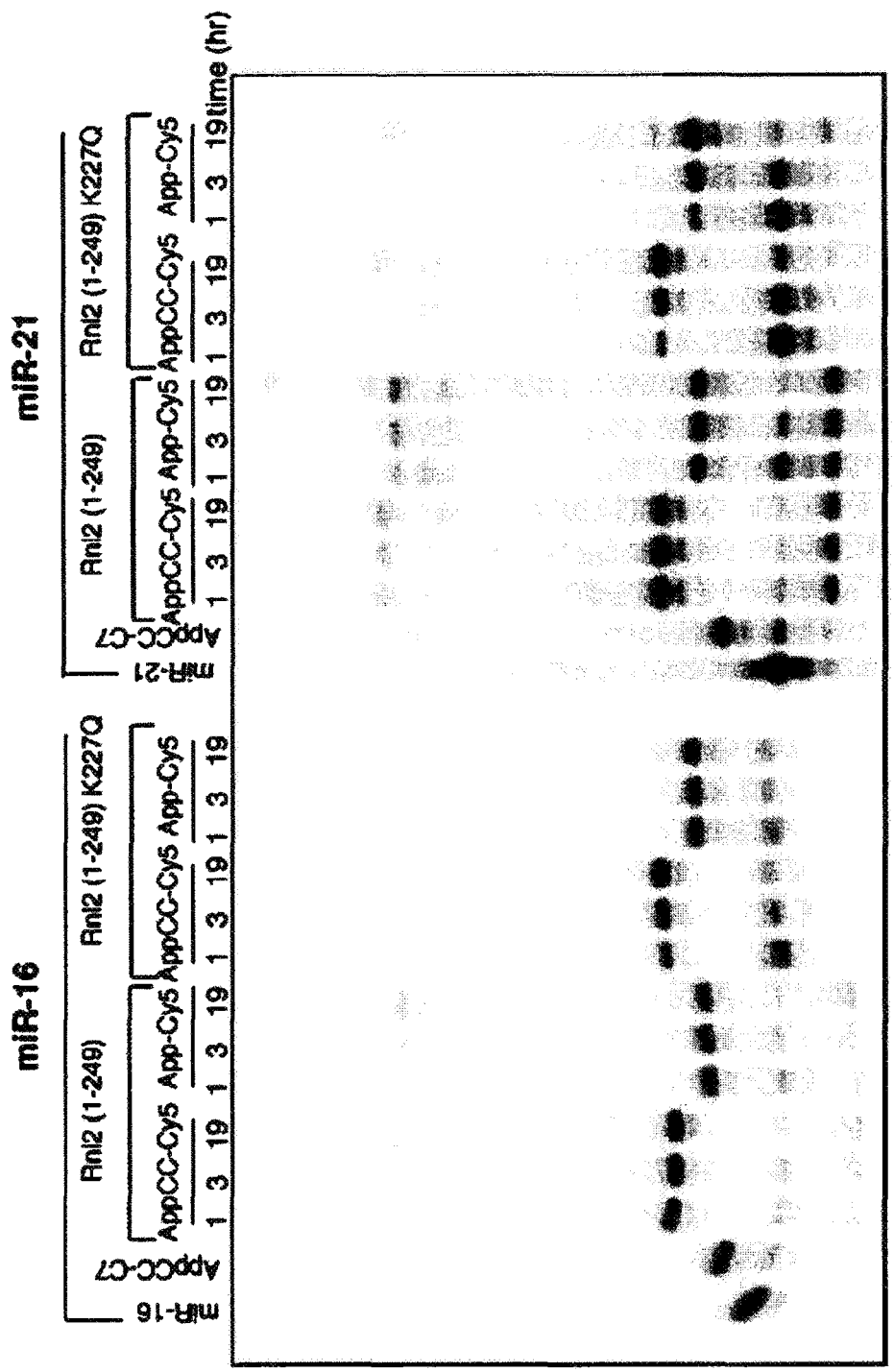
FIG. 7 is a gel showing a ligation reaction with fluorescent labeled donors using Rnl2(1-249) and Rnl2(1-249)K227Q.

FIG. 7 is a gel showing a ligation reaction with fluorescent labeled donors using Rnl2(1-249) and Rnl2(1-249)K227Q. Reaction conditions were described as in FIG. 2. The structure of the fluorescent Cy5-labeled pre-adenylated compounds is described in FIGS. 6A-H. As shown in FIG. 7, AppdCpC-c7-NH-dye donors are ligated with comparable efficiency to AppdCpC-c7-NH$_2$. As shown in FIG. 7 lane AppCy5, similar to other ligases, there is no requirement for having a nucleotide residue in the adenylated donor since ADP beta esters react in a comparable way.

Figure 11:
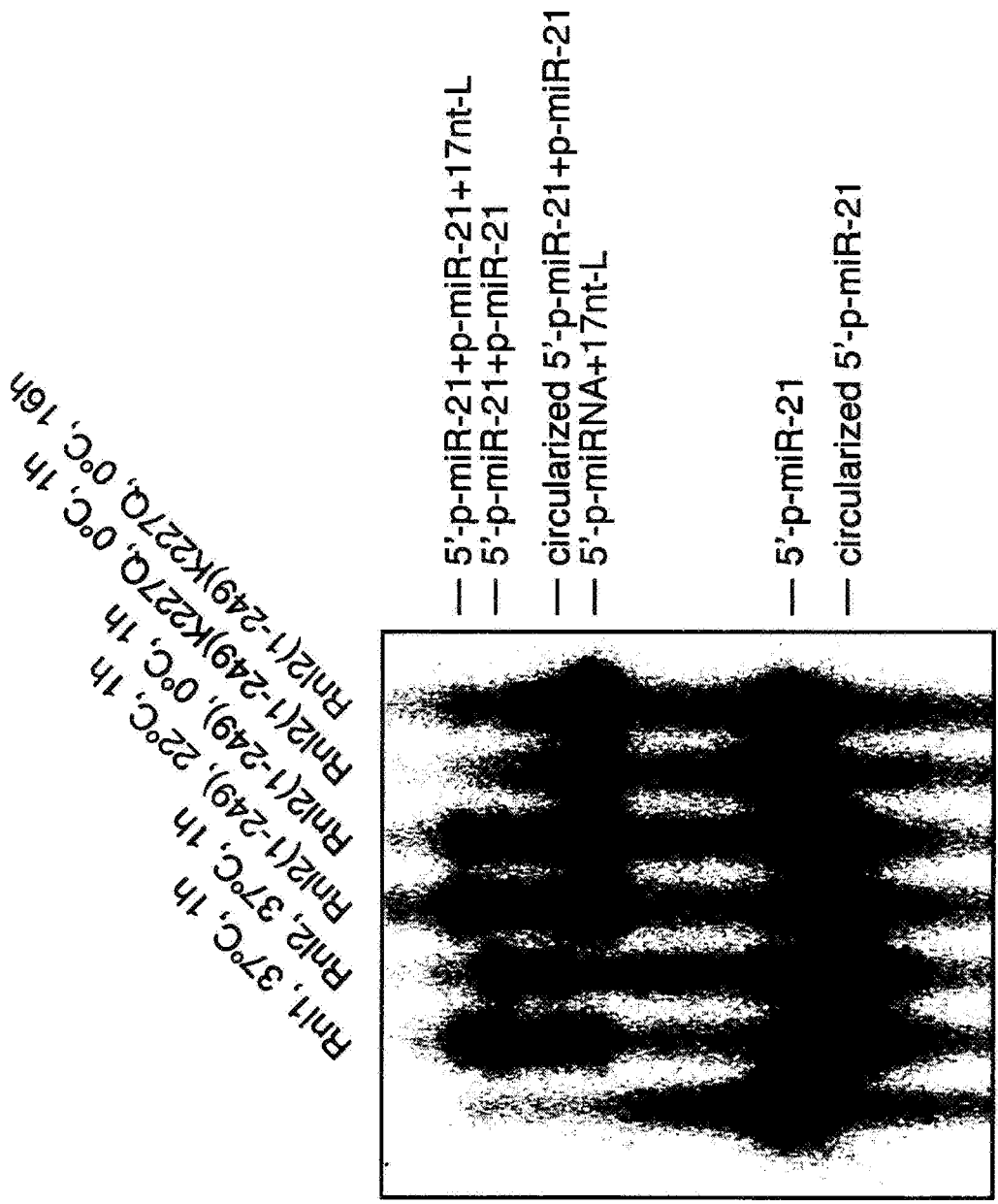
FIG. 11 is a gel showing the comparison of commercial ligases and Rnl2(1-249)K227Q in the 3'-labeling reaction of miR21 with a 3'-blocked 17-nt adenylated adapter oligonucleotide.

FIG. 11 is a gel showing the comparison of commercial ligases with Rnl2(1-249)K227Q in the 3'-labeling reaction of miR21 with a 3'-blocked 17-nt adenylated adapter oligonucleotide. Experimental conditions included the following: a concentration of donor (App-17-mer-3'-c$_7$NH$_2$), 1.25 µM acceptor, and 5'-p-miR21 100 Nm. All enzymes were used at 1.5 µM concentration under conditions described in FIG. 2. Reaction time and temperature were as follows: Rnl1, 37° C., 1 hr; Rnl2, 37° C., 1 hr; Rnl2 (1-249), 22° C., 1 hr; Rnl2 (1-249), 0° C., 1 hr; Rnl2 (1-249) K227Q, 0° C., 1 hr; Rnl2 (1-249) K227Q, 0° C., 16 hr.

In FIG. 11 circularization products were only observed with Rnl-1 and Rnl-2. The truncated Rnl2(1-249) gives a mixture of circularization and ligation products. The mutated truncated enzyme gives 37% ligation product after 1 hr at 0° C., and 80% ligation product after 17 hr incubation.

Chemical Synthesis of Pre-Adenylated Nucleotide Derivatives and Oligonucleotides For this reaction, 5'-adenylated oligonucleotides are required as donors. An efficient solution for solid phase adenylation reaction of oligonucleotides was also developed, which complements solid phase synthetic methods and allows the adenylation reaction to be performed with comparable efficiency to the usual coupling steps.

Solid phase synthesis of 5'-adenylated oligonucleotides have an advantage over usual solution methods in that commercially available amino CPG supports can be used for the synthesis of App-NN—NH$_2$ type compounds, which are suitable for post-synthetic labeling with reactive dye derivatives to obtain labeled donors for RNA labeling in the T4 RNA ligase catalyzed reaction.

It is difficult to carry out chemical adenylation reactions on the scale of oligonucleotide synthesis (1-10 μmol) in solution, and purification of the product mixtures obtained from conventional phosphoanhydride synthesis methods requires work intensive chromatography or gel-purification techniques.

The synthetic method of the invention is assisted by the oxidative amidation of oligonucleotide 5' H-phosphonates. This activation reaction can be performed very cleanly with trimethylsilylimidazol with support bound H-phosphonate derivatives, and the resulting 5' phosphorimidazolidate can be converted into the product with excess of AMP trioctylammonium salt in anhydrous DMF. The oligonucleotide H-phosphonates precursors are accessible on several routes. The use of salicylphosphochloridite for the phosphitylation of the 5' OH is preferred, because mild hydrolysis conditions are compatible with succinate solid supports. The yield of phosphitylation is usually higher then 90% when the reagent is used in 5-fold excess on 10 μmol scale. The inventors have found that these conditions are also suitable to work with standard 1 μmol synthesis columns.

Figure 10:
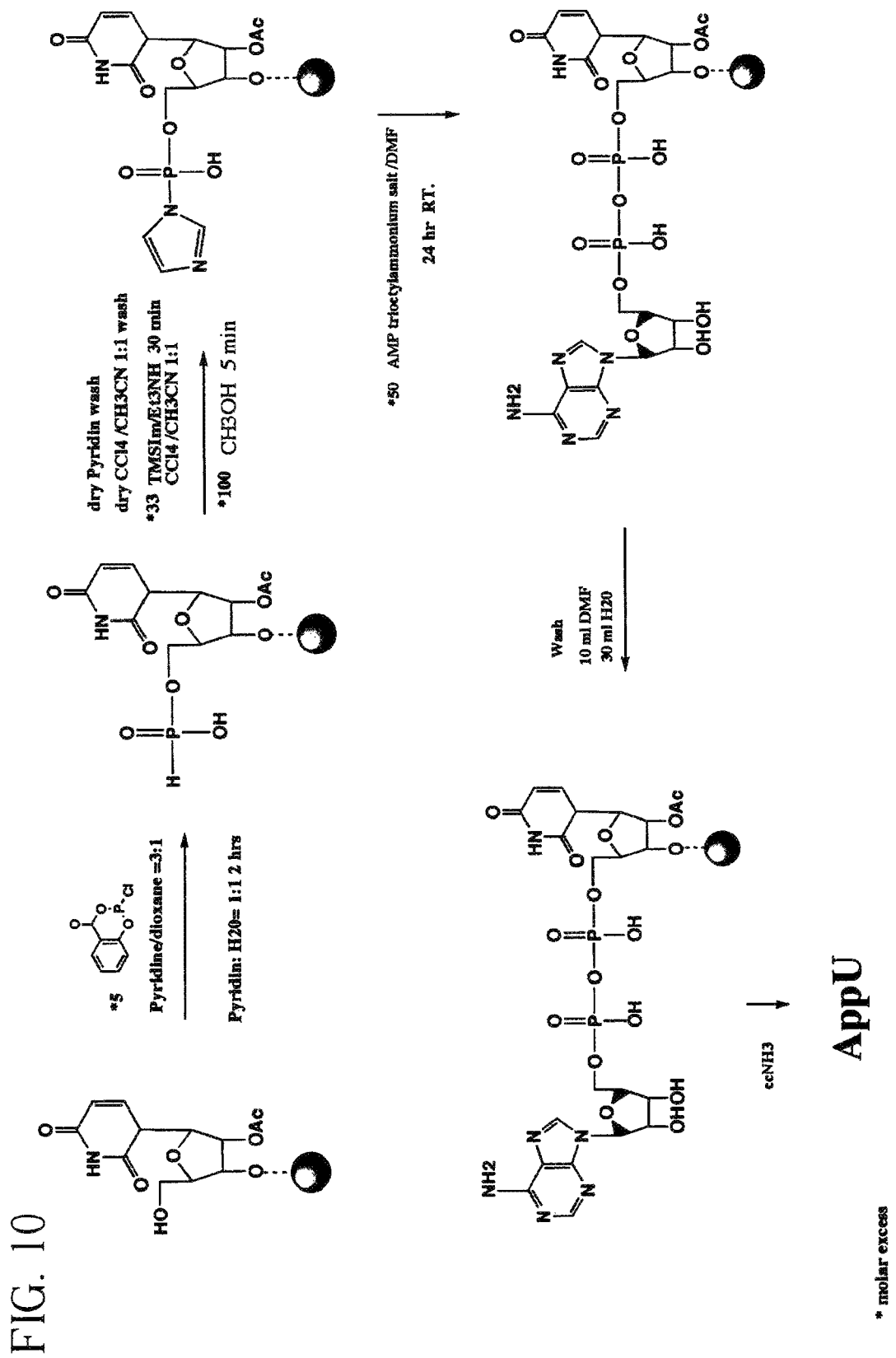
FIG. 10 is a schematic showing the details of the solid phase adenylation chemistry.

FIG. 10 presents details of the solid phase adenylation with AppU as an example. The 5' OH group of support-bound protected oligonucleotides was phosphitylated with salicylphosphochloridite and the resulting rimmers derivatives were hydrolyzed with pyridine-water to give oligonucleotide 5' H-phosphonates in excellent yield. Oxidative amidation of the H-phosphonate was performed with trimetylsilylimidazole in tetrachloromethane:acetonitrile (1:1) and the resulting support bound 5'-phosphorimidazolidates were reacted immediately with a 30- to 50-fold excess of AMP trioctylammonium salt in anhydrous DMF. Reaction for 24 h at room temperature resulted in the quantitative formation of the pyrophosphate derivatives as shown by thin layer chromatography of the reaction mixture. After washing the support-bound product with DMF, acetonitrile and water, the product was released from the support and base protecting groups were removed with concentrated aqueous ammonia.

Ligation of Donors with a Free 3'OH Group

When adenylated donors of the structure AppN are employed, with N as a ribonucleoside derivative with a free 3' OH group, the enzymes described above, such as Rnl2(1-249)K227Q, catalyze multiple incorporations of the N residue. The number of N residues incorporated is time dependent. Because the ligase has no specific structure requirement for N, this property of Rnl2(1-249)K227Q will allow the attachment of multiple labels to the 3' OH end of any phosphorylated oligoribonucleotide.

Figure 8:
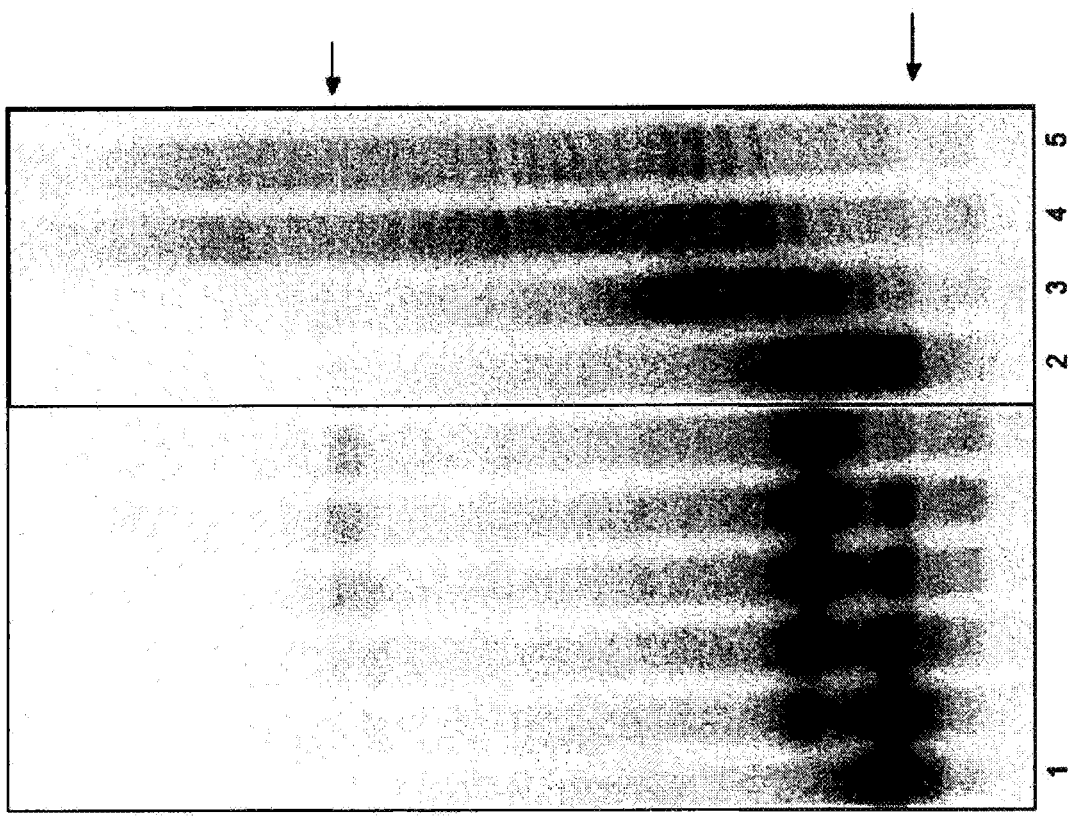
FIG. 8 is a gel showing multiple incorporation of Pu using AppU as donor with the Rnl2(1-249)K227Q mutant.

The multiple attachment of Pu using AppU as a donor with the Rnl2(1-249)K227Q mutant is shown in FIG. 8. Lane 1 shows miR-21. Lanes 2, 3, 4 show the reaction mixture after 1, 6, 24 h, respectively, under conditions of FIG. 2. Lane 5 shows the results after 24 h with repeated addition of the enzyme. The rimmers lanes represent a time course of ligation of AppdCpdC-c7-NH2 dimer and is not relevant for illustration of polymerization.

EXAMPLES

Example 1

Preparation of the Mutant RNA Ligase 2, Rnl2(1-249)K227Q

The Rnl2(1-249)K227Q mutant was generated using the QuikChange II XL kit (Stratagene). Purification of the mutant protein was performed as described (Ho et al. 2004). Briefly, 1 l culture of E. coli Rosetta 2 (DE3)/Pet16b-Rnl2(1-249) K227Q was grown at 37° C. in Luria-Bertani medium containing 0.1 mg/ml ampicillin until the $A_{600}$ reached 0.5. The culture was adjusted to 0.4 Mm isopropyl-D-thiogalactopyranoside (IPTG), and incubation was continued at 17° C. for 18 h. Cells were harvested by centrifugation, and the pellet was stored at −80° C. All subsequent procedures were performed at 4° C. Thawed bacteria were resuspended in 40 ml of buffer A (50 mM Tris-HCl, pH 7.5, 1 M NaCl, 15 mM imidazole, 10% sucrose). Lysozyme, PMSF, benzamidine, and Triton X-100 were added to final concentrations of 1 mg/ml, 0.2 mM, 1 mM, and 0.2%, respectively. The lysates were sonicated to reduce viscosity, and insoluble material was removed by centrifugation for 40 min at 17,000 rpm in a Sorvall SS34 rotor. The soluble extract was mixed with 2 ml of Ni-nitrilotriacetic acid-agarose (Qiagen) for 2 h with constant rotation. The resin was recovered by centrifugation, washed once with 40 ml of buffer A three times, and resuspended in 20 ml of buffer A. The slurry was poured into a column, washed sequentially with 5 ml of buffer A, 5 ml of 50 mM imidazole in buffer B (50 mM Tris-HCl, pH 7.5, 0.2 M NaCl, 10% glycerol), and 5 ml of 100 mM imidazole in buffer B Rnl2(1-249)K227Q was step-eluted with 5 ml 200 mM imidazole in buffer B. The polypeptide compositions of the eluate fractions were monitored by SDS-PAGE. The peak fractions were pooled and dialyzed against buffer containing 50 mM Tris-HCl, pH 8.0, 0.25 M NaCl, 1 mM DTT and 10% glycerol.

Example 2

Synthesis of Adenylated Donors 0.25 M AMP Solution in DMF:

To a stirred solution of AMP free acid (922 mg, 2.5 mmol) in 5 ml methanol, 1 equivalent tri-n-octylamine (1.09 ml) was added. A clear solution was obtained within 30 mM The solvent was evaporated to leave the product as white foam. The residue was coevaporated twice with 10 ml anhydrous DMF. The residue was then dissolved in 10 ml to give a 0.25 M solution.

Example 3

Procedure for Phosphitylation and Adenylation on 10 μmol Scale

For the synthesis of dimers or trimers reusable Twist columns were employed. Oligonucleotide synthesis was performed with 10 μmol CPG support loaded with ribonucleosides or with the aminolinker. After completion of the solid phase synthesis the synthesis column was washed twice with 5 ml dichloromethane, flushed with argon and dried overnight under vacuum. Then the CPG was washed with 5 ml dry dioxane-pyridine (3:1) and a syringe filled with 1 ml dioxane-pyridine (3:1) was attached to the top of the column. An empty syringe was attached to the bottom. Freshly prepared 1 M solution of 2-chloro-4H-1,2,3-dioxaphosphorin-4-one in anhydrous dioxane 50 μl (50 μmol) was injected into the top syringe. The dioxane-pyridine solution was moved between the two syringes for 10 min then occasionally for 30 min. The reaction was quenched with pyridine:water (1:1). After 3 h the column was flushed dry with argon, opened and a sample taken to test for the yield of phosphitylation after ammonia treatment. The column containing the 5'-H-phosphonate was washed three times with 5 ml dry pyridine followed by three washes with 5 ml of dry acetonitrile:tetrachloromethane (1:1). A syringe filled with 1 ml acetonitrile:tetrachloromethane (1:1) was attached to the top of the column and 330 μmol (44 μl) trimethylsilylimidazole followed by 330 μmol (42 μl) triethylamine was injected into the top syringe. Solvent with reagent was moved up and down for 10 min, after this time approximately once per 5 min After 30 min, 1 ml acetonitrile:tetrachloromethane (1:1) containing 1 mmol (40 μl methanol) was added with a syringe. After a 5 min period another syringe filled with 5 ml 0.25 M AMP trioctylammonium salt in DMF (see above) was placed on the top of the column and the DMF solution was pushed slowly through the column During this step, the heavier acetonitrile:tetrachloromethane (1:1) part is cleanly separated from the DMF and forms a sharp front. The AMP solution was kept in contact with the support for 24 h. The reaction was stopped by washing with 5 ml DMF to remove the AMP octylammonium salt, three washes of 5 ml methanol and three more washes of 5 ml water. After flushing the column with argon, the product was released from the column by treatment with concentrated 28% aqueous ammonia for 2 h. Base protecting groups where removed by heating for 5 h at 60° C. in a 1.5 ml screw cap tube, and ammonia was removed by evaporation on a Speed-Vac concentrator.

Product purity was checked by TLC using n-propanol-ammonia (28%)-water (11:7:2) as solvent or reverse phase HPLC. The retention time and product composition by HPLC were pdCpdC 8.63 min (7%), AppdCdC 9.89 min (75%), dCdC 10.35 min (16%).

The structures of the adenylated compounds were verified with $^{31}$P NMR.

REFERENCES

Aravin, A., and Tuschl, T. (2005). Identification and characterization of small RNAs involved in RNA silencing. FEBS Lett. 579, 5830-5840.

England, T. E., Gumport, R. I., and Uhlenbeck, O. C. (1977). Dinucleoside pyrophosphate are substrates for T4-induced RNA ligase. Proc. Natl. Acad. Sci. USA 74, 4839-4842.

Ho, C. K. and Shuman, S. 2002. Bacteriophage T4 RNA ligase 2 (gp24.1) exemplifies a family of RNA ligases found in all phylogenetic domains. Proc Natl Acad Sci USA 99(20): 12709-12714.

Ho, C. K., Wang, L. K., Lima, C. D., and Shuman, S. (2004). Structure and mechanism of RNA ligase. Structure (Camb) 12, 327-339.

Nandakumar, J., Ho, C. K., Lima, C. D., and Shuman, S. 2004. RNA substrate specificity and structure-guided mutational analysis of bacteriophage T4 RNA ligase 2. J Biol Chem 279(30): 31337-31347.

Pfeffer, S., Sewer, A., Lagos-Quintana, M., Sheridan, R., Sander, C., Zavolan, M., Grasser, F. A., van Dyk, L. F., Ho, C. K., Shuman, S., et al. (2005). Identification of microRNAs of the herpesvirus family. Nature Meth. 2, 269-276.

Pfeffer, S., Zavolan, M., Grasser, F. A., Chien, M., Russo, J. J., Ju, J., John, B., Enright, A. J., Marks, D., Sander, C., and Tuschl, T. (2004). Identification of virus-encoded microRNAs. Science 304, 734-736.

Yin S, Ho C K, Shuman S. (2003). Structure-function analysis of T4 RNA ligase 2. J Biol Chem. 278, 17601-17608.

---

What is claimed is:

1. A method for enzymatically ligating a pre-adenylated donor molecule to RNA, the method comprising reacting the pre-adenylated donor molecule and the 3' hydroxyl group of a 5' phosphorylated or de-phosphorylated RNA in the absence of adenosine triphosphate and in the presence of an enzyme comprising a truncated T4 RNA ligase 2 (1-249), wherein said enzyme includes a substitution of a lysine with an arginine at a position corresponding to position 225 as encoded by SEQ ID. NO: 3, and wherein the truncated T4 RNA ligase 2 is capable of ligating the pre-adenylated donor molecule to the 3' hydroxyl group of the optionally de-phosphorylated RNA in the absence of adenosine triphosphate.

2. The method according to claim 1, wherein said RNA is dephosphorylated.

3. The method according to claim 1, wherein said RNA is microRNA.

4. The method according to claim 1, wherein said donor molecule has formula:

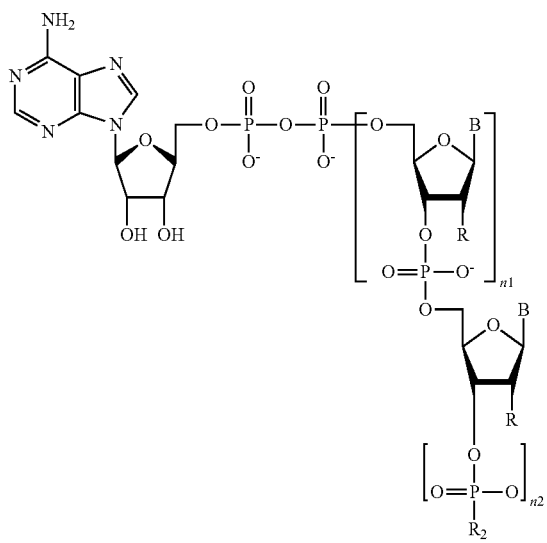

wherein,
n1=0-25;
R represents H, OH, $OCH_3$, $O(CH_2)_2OCH_3$, F, $NH_2$;
B represents a natural nucleic acid base or base analog, and
when n2=0, $R_2$ represents H, $NH_2$, NHQ, $-(CH_2)_nNH_2$, or an aminoalkyl linker having a formula $-(CH_2)_nNHQ$, $-O(CH_2)_nNH_2$, $-O(CH_2)_nNHQ$, wherein n=2 to 18; wherein the alkyl chains represented as $(CH_2)_n$ are optionally substituted with one or more hydroxymethyl groups; and wherein Q represents an active moiety; and when n2=1, $R_2$ represents an aminoalkyl linker having a formula $-O(CH_2)_nNH_2$ or $-O(CH_2)_nNHQ$, wherein n=2 to 18; wherein the alkyl chains represented as $(CH_2)_n$ are optionally substituted with one or more hydroxymethyl groups; and wherein Q represents an active moiety.

5. The method according to claim 4, wherein n=2 to 6.

6. The method according to claim 4, wherein n1=0 to 3; R represents H; B represents cytosine, uridine, thymidine, or adenosine; and $R_2$ represents $-OCH_2CH-(CH_2OH)(CH_2)_4NH_2$ or $-CH_2CH-(CH_2OH)(CH_2)_4NHQ$.

7. The method according to claim 6, wherein B represents cytosine.

8. The method according to claim 4, wherein the active moiety is a dye.

9. The method according to claim 4, wherein the active moiety is an organic dye.

10. The method according to claim 9, wherein the organic dye is Cy5, Cy3 or fluorescein.

11. The method according to claim 4, wherein the active moiety is a member of a specific molecular binding pair.

12. The method according to claim 11, wherein the member of a specific molecular binding pair is biotin or digoxigenin.

13. The method according to claim 11, wherein the member of a specific molecular binding pair comprises an antigen.

14. The method according to claim 11, wherein the member of a specific molecular binding pair comprises a binding domain of a monoclonal antibody.

15. The method according to claim 14, wherein the binding domain of a monoclonal antibody is a single chain antibody.

16. The method according to claim 4, wherein the active molecule is cholesterol.

17. The method according to claim 4 wherein said ligating is conducted at a minimum temperature of about 0° C.

18. The method according to claim 4 wherein said ligating is conducted at a maximum temperature of about 25° C.

19. The method according to claim 18 wherein the maximum temperature is about 22° C.

20. The method according to claim 18 wherein the maximum temperature is about 10° C.

21. The method according to claim 1, wherein said donor molecule has formula

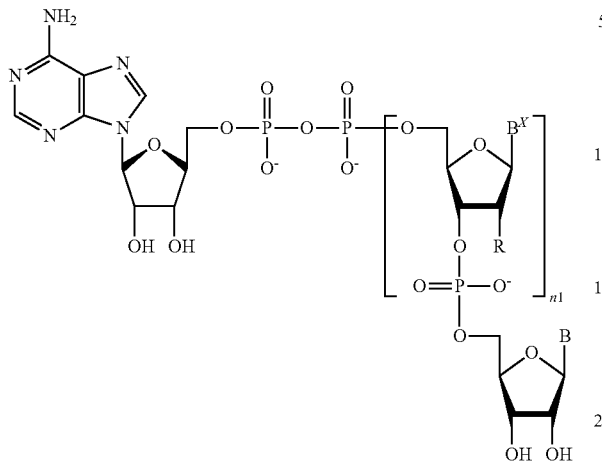

wherein, n1=0-25;

R represents H, OH, OCH₃, O(CH₂)₂OCH₃, F, NH₂;

B represents a natural nucleic acid base or base analog,

X represents —(CH₂)ₙNH₂, —(CH₂)ₙNHQ-, —CH=CH—CH—NH₂, —CH=CH—CH—NHQ, —CH=CH—C(=O)—NH—(CH₂)ₙNH₂, —CH=CH—C(=O)—NH—(CH₂)ₙNH₂-Q, wherein n=2 to 18, or a nucleotide having a pyrimidine base, said nucleotide carrying an aminolinker at a 5-position of the pyrimidine base; and wherein Q respresents an active moiety.

22. The method according to claim 21 wherein n1=0-3; R represents H; B represents cytosine, uridine, thymidine, or adenosine; and n=3 to 6.

23. The method according to claim 22, wherein B represents cytosine.

24. The method according to claim 1, wherein said donor molecule has formula

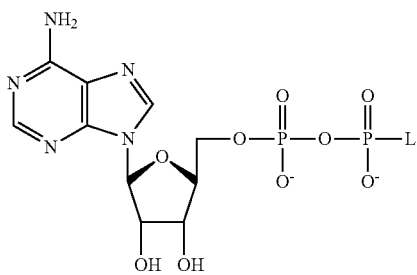

wherein L represents an aminoalkyl linker having a formula —O(CH₂)ₙ—NH₂ or —O(CH₂)ₙ—NHQ, wherein n=3 to 6; and Q represents an active moiety.

* * * * *

SEQUENCE LISTING

```
<160> NUMBER OF SEQ ID NOS: 3

<210> SEQ ID NO 1
<211> LENGTH: 334
<212> TYPE: PRT
<213> ORGANISM: Homo sapiens

<400> SEQUENCE: 1

Met Phe Lys Lys Tyr Ser Ser Leu Glu Asn His Tyr Asn Ser Lys Phe
1               5                   10                  15

Ile Glu Lys Leu Tyr Ser Leu Gly Leu Thr Gly Gly Glu Trp Val Ala
            20                  25                  30

Arg Glu Lys Ile His Gly Thr Asn Phe Ser Leu Ile Ile Glu Arg Asp
        35                  40                  45

Lys Val Thr Cys Ala Lys Arg Thr Gly Pro Ile Leu Pro Ala Glu Asp
    50                  55                  60

Phe Phe Gly Tyr Glu Ile Ile Leu Lys Asn Tyr Ala Asp Ser Ile Lys
65                  70                  75                  80

Ala Val Gln Asp Ile Met Glu Thr Ser Ala Val Val Ser Tyr Gln Val
                85                  90                  95

Phe Gly Glu Phe Ala Gly Pro Gly Ile Gln Lys Asn Val Asp Tyr Cys
            100                 105                 110

Asp Lys Asp Phe Tyr Val Phe Asp Ile Ile Val Thr Thr Glu Ser Gly
        115                 120                 125

Asp Val Thr Tyr Val Asp Asp Tyr Met Met Glu Ser Phe Cys Asn Thr
    130                 135                 140

Phe Lys Phe Lys Met Ala Pro Leu Leu Gly Arg Gly Lys Phe Glu Glu
145                 150                 155                 160
```

```
Leu Ile Lys Leu Pro Asn Asp Leu Asp Ser Val Val Gln Asp Tyr Asn
            165                 170                 175

Phe Thr Val Asp His Ala Gly Leu Val Asp Ala Asn Lys Cys Val Trp
        180                 185                 190

Asn Ala Glu Ala Lys Gly Glu Val Phe Thr Ala Glu Gly Tyr Val Leu
            195                 200                 205

Lys Pro Cys Tyr Pro Ser Trp Leu Arg Asn Gly Asn Arg Val Ala Ile
        210                 215                 220

Lys Cys Lys Asn Ser Lys Phe Ser Glu Lys Lys Ser Asp Lys Pro
225                 230                 235                 240

Ile Lys Ala Lys Val Glu Leu Ser Glu Ala Asp Asn Lys Leu Val Gly
            245                 250                 255

Ile Leu Ala Cys Tyr Val Thr Leu Asn Arg Val Asn Asn Val Ile Ser
        260                 265                 270

Lys Ile Gly Glu Ile Gly Pro Lys Asp Phe Gly Lys Val Met Gly Leu
            275                 280                 285

Thr Val Gln Asp Ile Leu Glu Glu Thr Ser Arg Glu Gly Ile Thr Leu
        290                 295                 300

Thr Gln Ala Asp Asn Pro Ser Leu Ile Lys Lys Glu Leu Val Lys Met
305                 310                 315                 320

Val Gln Asp Val Leu Arg Pro Ala Trp Ile Glu Leu Val Ser
            325                 330

<210> SEQ ID NO 2
<211> LENGTH: 6456
<212> TYPE: DNA
<213> ORGANISM: Artificial Sequence
<220> FEATURE:
<223> OTHER INFORMATION: Synthetic Sequence

<400> SEQUENCE: 2
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccgtactgcc gggcctctt     180 gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atccttattc tgatagctca actttagctt taataggctt     360
atcagacttt ttcttttcac taaatttaga gttcttgcat ttaatcgcta cacgatttcc     420
attacgaagc caagaaggat aacaaggttt caatacatat ccttcagcag taaatacttc     480
gccttttgct tcggcattcc aaacgcattt atttgcatca actaatccag catggtctac     540
tgtaaaatta taatcttgga cgacagaatc taaatcattt ggcaatttaa taagctcttc     600
aaatttaccg cgacctaaaa gtggagccat tttaaattta aatgtattac agaatgattc     660
catcatataa tcatctacat aagtcacatc accgctttct gtagtaacaa taatgtcaaa     720
tacataaaaa tctttatcac aataatcaac attcttctga atgccaggtc agcgaattc     780 gccaaagact tgataagata caaccgctga ggtttccata atatcttgta cagctttaat     840
ggaatcagca taattcttca aaataatttc atacccaaag aaatcttcag caggaagaat     900
cggtccagtg cgtttagcgc aagtcacttt atcacgctca ataatcaatg agaaatttgt     960
gccgtgaatc ttttcacgag ctacccactc cccaccagtc aatcccaagc tataaagttt    1020
ttcaataaat ttagagttgt aatgattttc aagactgcta tacttttaa acatcatatg    1080
```

```
acgaccttcg atatggccgc tgctgtgatg atgatgatga tgatgatgat gatggcccat    1140
ggtatatctc cttcttaaag ttaaacaaaa ttatttctag aggggaattg ttatccgctc    1200
acaattcccc tatagtgagt cgtattaatt tcgcgggatc gagatctcga tcctctacgc    1260
cggacgcatc gtggccggca tcaccggcgc acaggtgcg gttgctggcg cctatatcgc     1320
cgacatcacc gatggggaag atcgggctcg ccacttcggg ctcatgagcg cttgtttcgg    1380
cgtgggtatg gtggcaggcc ccgtggccgg gggactgttg ggcgccatct ccttgcatgc    1440
accattcctt gcggcggcgg tgctcaacgg cctcaaccta ctactgggct gcttcctaat    1500
gcaggagtcg cataagggag agcgtcgaga tcccggacac catcgaatgg cgcaaaacct    1560
ttcgcggtat ggcatgatag cgcccggaag agagtcaatt cagggtggtg aatgtgaaac    1620
cagtaacgtt atacgatgtc gcagagtatg ccggtgtctc ttatcagacc gtttcccgcg    1680
tggtgaacca ggccagccac gtttctgcga aaacgcggga aaaagtggaa gcggcgatgg    1740
cggagctgaa ttacattccc aaccgcgtgg cacaacaact ggcgggcaaa cagtcgttgc    1800
tgattggcgt tgccacctcc agtctggccc tgcacgcgcc gtcgcaaatt gtcgcggcga    1860
ttaaatctcg cgccgatcaa ctgggtgcca gcgtggtggt gtcgatggta aacgaagcg     1920 gcgtcgaagc ctgtaaagcg gcggtgcaca atcttctcgc gcaacgcgtc agtgggctga    1980
tcattaacta tccgctggat gaccaggatg ccattgctgt ggaagctgcc tgcactaatg    2040
ttccggcgtt atttcttgat gtctctgacc agacacccat caacagtatt attttctccc    2100
atgaagacgg tacgcgactg ggcgtggagc atctggtcgc attgggtcac cagcaaatcg    2160
cgctgttagc gggcccatta agttctgtct cggcgcgtct gcgtctggct ggctggcata    2220
aatatctcac tcgcaatcaa attcagccga tagcggaacg ggaaggcgac tggagtgcca    2280
tgtccggttt tcaacaaacc atgcaaatgc tgaatgaggg catcgttccc actgcgatgc    2340
tggttgccaa cgatcagatg gcgctgggcg caatgcgcgc cattaccgag tccgggctgc    2400
gcgttggtgc ggatatctcg gtagtgggat acgacgatac cgaagacagc tcatgttata    2460
tcccgccgtt aaccaccatc aaacaggatt ttcgcctgct ggggcaaacc agcgtggacc    2520
gcttgctgca actctctcag ggccaggcgg tgaaggcaa tcagctgttg cccgtctcac      2580
tggtgaaaag aaaaaccacc ctggcgccca atacgcaaac cgcctctccc cgcgcgttgg    2640
ccgattcatt aatgcagctg gcacgacagg tttcccgact ggaaagcggg cagtgagcgc    2700
aacgcaatta atgtaagtta gctcactcat taggcaccgg gatctcgacc gatgcccttg    2760
agagccttca acccagtcag ctccttccgg tgggcgcggg gcatgactat cgtcgccgca    2820
cttatgactg tcttctttat catgcaactc gtaggacagg tgccggcagc gctctgggtc    2880
attttcggcg aggaccgctt tcgctggagc gcgacgatga tcggcctgtc gcttgcggta    2940
ttcggaatct tgcacgccct cgctcaagcc ttcgtcactg gtcccgccac caaacgtttc    3000
ggcgagaagc aggccattat cgccggcatg gcggccgacg cgctgggcta cgtcttgctg    3060
gcgttcgcga cgcgaggctg gatggccttc cccattatga ttcttctcgc ttccggcggc    3120
atcgggatgc ccgcgttgca ggccatgctg tccaggcagg tagatgacga ccatcaggga    3180
cagcttcaag gatcgctcgc ggctcttacc agcctaactt cgatcactgg accgctgatc    3240
gtcacggcga tttatgccgc ctcggcgagc acatggaacg ggttggcatg gattgtaggc    3300
gccgccctat accttgtctg cctccccgcg ttgcgtcgcg gtgcatggag ccgggccacc    3360
tcgacctgaa tggaagccgg cggcacctcg ctaacggatt caccactcca gaattggag    3420 ccaatcaatt cttgcggaga actgtgaatg cgcaaaccaa cccttggcag aacatatcca    3480
```

```
tcgcgtccgc catctccagc agccgcacgc ggcgcatctc gggcagcgtt gggtcctggc   3540
cacgggtgcg catgatcgtg ctcctgtcgt tgaggacccg gctaggctgg cggggttgcc   3600
ttactggtta gcagaatgaa tcaccgatac gcgagcgaac gtgaagcgac tgctgctgca   3660
aaacgtctgc gacctgagca acaacatgaa tggtcttcgg tttccgtgtt tcgtaaagtc   3720
tggaaacgcg gaagtcagcg ccctgcacca ttatgttccg gatctgcatc gcaggatgct   3780
gctggctacc ctgtggaaca cctacatctg tattaacgaa gcgctggcat tgaccctgag   3840
tgattttcct ctggtcccgc cgcatccata ccgccagttg tttaccctca caacgttcca   3900
gtaaccggga atgttcatca tcagtaaccc gtatcgtgag catcctctct cgtttcatcg   3960
gtatcattac ccccatgaac agaaatcccc cttacacgga ggcatcagtg accaaacagg   4020
aaaaaaccgc ccttaacatg gcccgcttta tcagaagcca gacattaacg cttctggaga   4080
aactcaacga gctggacgcg gatgaacagg cagacatctg tgaatcgctt cacgaccacg   4140
ctgatgagct ttaccgcagc tgcctcgcgc gtttcggtga tgacggtgaa aacctctgac   4200
acatgcagct cccggagacg gtcacagctt gtctgtaagc ggatgccggg agcagacaag   4260
cccgtcaggg cgcgtcagcg ggtgttggcg ggtgtcgggg cgcagccatg acccagtcac   4320
gtagcgatag cggagtgtat actggcttaa ctatgcggca tcagagcaga ttgtactgag   4380
agtgcaccat atatgcggtg tgaaataccg cacagatgcg taaggagaaa ataccgcatc   4440
aggcgctctt ccgcttcctc gctcactgac tcgctgcgct cggtcgttcg gctgcggcga   4500
gcggtatcag ctcactcaaa ggcggtaata cggttatcca cagaatcagg ggataacgca   4560
ggaaagaaca tgtgagcaaa aggccagcaa aaggccagga accgtaaaaa ggccgcgttg   4620
ctggcgtttt tccataggct ccgcccccct gacgagcatc acaaaaatcg acgctcaagt   4680
cagaggtggc gaaacccgac aggactataa agataccagg cgtttccccc tggaagctcc   4740
ctcgtgcgct ctcctgttcc gaccctgccg cttaccggat acctgtccgc ctttctccct   4800
tcgggaagcg tggcgctttc tcatagctca cgctgtaggt atctcagttc ggtgtaggtc   4860
gttcgctcca agctgggctg tgtgcacgaa ccccccgttc agcccgaccg ctgcgcctta   4920
tccggtaact atcgtcttga gtccaacccg gtaagacacg acttatcgcc actggcagca   4980
gccactggta acaggattag cagagcgagg tatgtaggcg gtgctacaga gttcttgaag   5040
tggtggccta actacggcta cactagaagg acagtatttg gtatctgcgc tctgctgaag   5100
ccagttacct tcggaaaaag agttggtagc tcttgatccg gcaaacaaac caccgctggt   5160
agcggtggtt tttttgtttg caagcagcag attacgcgca gaaaaaaagg atctcaagaa   5220
gatcctttga tcttttctac ggggtctgac gctcagtgga acgaaaactc acgttaaggg   5280
attttggtca tgagattatc aaaaaggatc ttcacctaga tccttttaaa ttaaaaatga   5340
agttttaaat caatctaaag tatatatgag taaacttggt ctgacagtta ccaatgctta   5400
atcagtgagg cacctatctc agcgatctgt ctatttcgtt catccatagt tgcctgactc   5460
cccgtcgtgt agataactac gatacgggag ggcttaccat ctggccccag tgctgcaatg   5520
ataccgcgag acccacgctc accggctcca gatttatcag caataaacca gccagcggaa   5580
agggccgagc gcagaagtgg tcctgcaact ttatccgcct ccatccagtc tattaattgt   5640
tgccgggaag ctagagtaag tagttcgcca gttaatagtt tgcgcaacgt tgttgccatt   5700
gctgcaggca tcgtggtgtc acgctcgtcg tttggtatgg cttcattcag ctccggttcc   5760
caacgatcaa ggcgagttac atgatccccc atgttgtgca aaaaagcggt tagctccttc   5820
```

```
ggtcctccga tcgttgtcag aagtaagttg gccgcagtgt tatcactcat ggttatggca    5880
gcactgcata attctcttac tgtcatgcca tccgtaagat gcttttctgt gactggtgag    5940
tactcaacca agtcattctg agaatagtgt atgcggcgac cgagttgctc ttgcccggcg    6000
tcaacacggg ataataccgc gccacatagc agaactttaa aagtgctcat cattggaaaa    6060
cgttcttcgg ggcgaaaact ctcaaggatc ttaccgctgt tgagatccag ttcgatgtaa    6120
cccactcgtg cacccaactg atcttcagca tcttttactt tcaccagcgt ttctgggtga    6180
gcaaaaacag gaaggcaaaa tgccgcaaaa aagggaataa gggcgacacg gaaatgttga    6240
atactcatac tcttcctttt tcaatattat tgaagcattt atcagggtta ttgtctcatg    6300
agcggataca tatttgaatg tatttagaaa aataaacaaa taggggttcc gcgcacattt    6360
ccccgaaaag tgccacctga cgtctaagaa accattatta tcatgacatt aacctataaa    6420
aataggcgta tcacgaggcc ctttcgtctt caagaa                              6456

<210> SEQ ID NO 3
<211> LENGTH: 6456
<212> TYPE: DNA
<213> ORGANISM: Artificial Sequence
<220> FEATURE:
<223> OTHER INFORMATION: Synthetic Sequence

<400> SEQUENCE: 3
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccgtactgcc gggcctctt     180 gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atccttattc tgatagctca actttagctt taataggctt     360
atcagacttt ttcttttcac taaatttaga gttctggcat ttaatcgcta cacgatttcc     420
attacgaagc caagaaggat aacaaggttt caatacatat ccttcagcag taaatacttc     480 gcctttgct tcggcattcc aaacgcattt atttgcatca actaatccag catggtctac     540
tgtaaaatta atctctgga cgacagaatc taaatcattt ggcaatttaa taagctcttc     600
aaatttaccg cgacctaaaa gtggagccat tttaaattta aatgtattac agaatgattc     660
catcatataa tcatctacat aagtcacatc accgctttct gtagtaacaa taatgtcaaa     720
tacataaaaa tctttatcac cataatcaac attcttctga atgccaggtc cagcgaattc     780
gccaaagact tgataagata caaccgctga ggtttccata atatcttgta cagctttaat     840
ggaatcagca taattcttca aaataatttc atacccaaag aaatcttcag caggaagaat     900
cggtccagtg cgtttagcgc aagtcacttt atcacgctca ataatcaatg agaaatttgt     960
gccgtgaatc ttttcacgag ctacccactc cccaccagtc aatcccaagc tataaagttt    1020
ttcaataaat ttagagttgt aatgattttc aagactgcta tactttttaa acatcatatg    1080
acgaccttcg atatggccgc tgctgtgatg atgatgatga tgatgatgat gatggcccat    1140
ggtatatctc cttcttaaag ttaaacaaaa ttatttctag aggggaattg ttatccgctc    1200
acaattcccc tatagtgagt cgtattaatt tcgcgggatc gagatctcga tcctctacgc    1260
cggacgcatc gtggccggca tcaccggcgc cacaggtgcg gttgctggcg cctatatcgc    1320
cgacatcacc gatggggaag atcgggctcg ccacttcggg ctcatgagcg cttgtttcgg    1380
cgtgggtatg gtggcaggcc ccgtggccgg gggactgttg ggcgccatct ccttgcatgc    1440
```

```
accattcctt gcggcggcgg tgctcaacgg cctcaaccta ctactgggct gcttcctaat    1500
gcaggagtcg cataagggag agcgtcgaga tcccggacac catcgaatgg cgcaaaacct    1560
ttcgcggtat ggcatgatag cgcccggaag agagtcaatt cagggtggtg aatgtgaaac    1620
cagtaacgtt atacgatgtc gcagagtatg ccggtgtctc ttatcagacc gtttcccgcg    1680
tggtgaacca ggccagccac gtttctgcga aaacgcggga aaagtggaa gcggcgatgg     1740 cggagctgaa ttacattccc aaccgcgtgg cacaacaact ggcgggcaaa cagtcgttgc    1800
tgattggcgt tgccacctcc agtctggccc tgcacgcgcc gtcgcaaatt gtcgcggcga    1860
ttaaatctcg cgccgatcaa ctgggtgcca gcgtggtggt gtcgatggta gaacgaagcg    1920
gcgtcgaagc ctgtaaagcg gcggtgcaca atcttctcgc gcaacgcgtc agtgggctga    1980
tcattaacta tccgctggat gaccaggatg ccattgctgt ggaagctgcc tgcactaatg    2040
ttccggcgtt atttcttgat gtctctgacc agacacccat caacagtatt attttctccc    2100
atgaagacgg tacgcgactg ggcgtggagc atctggtcgc attgggtcac cagcaaatcg    2160
cgctgttagc gggcccatta agttctgtct cggcgcgtct gcgtctggct ggctggcata    2220
aatatctcac tcgcaatcaa attcagccga tagcggaacg ggaaggcgac tggagtgcca    2280
tgtccggttt tcaacaaacc atgcaaatgc tgaatgaggg catcgttccc actgcgatgc    2340
tggttgccaa cgatcagatg gcgctgggcg caatgcgcgc cattaccgag tccgggctgc    2400
gcgttggtgc ggatatctcg gtagtgggat acgacgatac cgaagacagc tcatgttata    2460
tcccgccgtt aaccaccatc aaacaggatt ttcgcctgct ggggcaaacc agcgtggacc    2520
gcttgctgca actctctcag ggccaggcgg tgaagggcaa tcagctgttg cccgtctcac    2580
tggtgaaaag aaaaaccacc ctggcgccca atacgcaaac cgcctctccc cgcgcgttgg    2640
ccgattcatt aatgcagctg gcacgacagg tttcccgact ggaaagcggg cagtgagcgc    2700
aacgcaatta atgtaagtta gctcactcat taggcaccgg gatctcgacc gatgcccttg    2760
agagccttca acccagtcag ctccttccgg tgggcgcggg gcatgactat cgtcgccgca    2820
cttatgactg tcttctttat catgcaactc gtaggacagg tgccggcagc gctctgggtc    2880
attttcggcg aggaccgctt tcgctggagc gcgacgatga tcggcctgtc gcttgcggta    2940
ttcggaatct tgcacgccct cgctcaagcc ttcgtcactg gtcccgccac caaacgtttc    3000
ggcgagaagc aggccattat cgccggcatg gcggccgacg cgctgggcta cgtcttgctg    3060
gcgttcgcga cgcgaggctg gatggccttc cccattatga ttcttctcgc ttccggcggc    3120
atcgggatgc ccgcgttgca ggccatgctg tccaggcagg tagatgacga ccatcaggga    3180
cagcttcaag gatcgctcgc ggctcttacc agcctaactt cgatcactgg accgctgatc    3240
gtcacggcga tttatgccgc ctcggcgagc acatggaacg ggttggcatg gattgtaggc    3300
gccgccctat accttgtctg cctccccgcg ttgcgtcgcg gtgcatggag ccgggccacc    3360
tcgacctgaa tggaagccgg cggcacctcg ctaacggatt caccactcca gaattggag     3420 ccaatcaatt cttgcggaga actgtgaatg cgcaaaccaa cccttggcag aacatatcca    3480
tcgcgtccgc catctccagc agccgcacgc ggcgcatctc gggcagcgtt gggtcctggc    3540
cacgggtgcg catgatcgtg ctcctgtcgt tgaggacccg gctaggctgg cggggttgcc    3600
ttactggtta gcagaatgaa tcaccgatac gcgagcgaac gtgaagcgac tgctgctgca    3660
aaacgtctgc gacctgagca acaacatgaa tggtcttcgg tttccgtgtt tcgtaaagtc    3720
tggaaacgcg gaagtcagcg ccctgcacca ttatgttccg gatctgcatc gcaggatgct    3780
```

```
gctggctacc ctgtggaaca cctacatctg tattaacgaa gcgctggcat tgaccctgag    3840
tgatttttct ctggtcccgc cgcatccata ccgccagttg tttaccctca caacgttcca    3900
gtaaccgggc atgttcatca tcagtaaccc gtatcgtgag catcctctct cgtttcatcg    3960
gtatcattac ccccatgaac agaaatcccc cttacacgga ggcatcagtg accaaacagg    4020
aaaaaaccgc ccttaacatg gcccgcttta tcagaagcca gacattaacg cttctggaga    4080
aactcaacga gctggacgcg gatgaacagg cagacatctg tgaatcgctt cacgaccacg    4140
ctgatgagct ttaccgcagc tgcctcgcgc gtttcggtga tgacggtgaa aacctctgac    4200
acatgcagct cccggagacg tcacagcttg tctgtaagcg gatgccggga gcagacaag    4260 cccgtcaggg cgcgtcagcg ggtgttggcg ggtgtcgggg cgcagccatg acccagtcac    4320
gtagcgatag cggagtgtat actggcttaa ctatgcggca tcagagcaga ttgtactgag    4380
agtgcaccat atatgcggtg tgaaataccg cacagatgcg taaggagaaa ataccgcatc    4440
aggcgctctt ccgcttcctc gctcactgac tcgctgcgct cggtcgttcg gctgcggcga    4500
gcggtatcag ctcactcaaa ggcggtaata cggttatcca cagaatcagg ggataacgca    4560
ggaaagaaca tgtgagcaaa aggccagcaa aaggccagga accgtaaaaa ggccgcgttg    4620
ctggcgtttt tccataggct ccgcccccct gacgagcatc acaaaaatcg acgctcaagt    4680
cagaggtggc gaaacccgac aggactataa agataccagg cgtttccccc tggaagctcc    4740
ctcgtgcgct ctcctgttcc gaccctgccg cttaccggat acctgtccgc ctttctccct    4800
tcgggaagcg tggcgctttc tcatagctca cgctgtaggt atctcagttc ggtgtaggtc    4860
gttcgctcca agctgggctg tgtgcacgaa ccccccgttc agcccgaccg ctgcgcctta    4920
tccggtaact atcgtcttga gtccaacccg gtaagacacg acttatcgcc actggcagca    4980
gccactggta acaggattag cagagcgagg tatgtaggcg gtgctacaga gttcttgaag    5040
tggtggccta actacggcta cactagaagg acagtatttg gtatctgcgc tctgctgaag    5100
ccagttacct tcggaaaaag agttggtagc tcttgatccg gcaaacaaac caccgctggt    5160
agcggtggtt tttttgtttg caagcagcag attacgcgca gaaaaaaagg atctcaagaa    5220
gatcctttga tcttttctac ggggtctgac gctcagtgga acgaaaactc acgttaaggg    5280
attttggtca tgagattatc aaaaaggatc ttcacctaga tccttttaaa ttaaaaatga    5340
agttttaaat caatctaaag tatatatgag taaacttggt ctgacagtta ccaatgctta    5400
atcagtgagg cacctatctc agcgatctgt ctatttcgtt catccatagt tgcctgactc    5460
cccgtcgtgt agataactac gatacgggag ggcttaccat ctggccccag tgctgcaatg    5520
ataccgcgag acccacgctc accggctcca gatttatcag caataaacca gccagccgga    5580
agggccgagc gcagaagtgg tcctgcaact ttatccgcct ccatccagtc tattaattgt    5640
tgccgggaag ctagagtaag tagttcgcca gttaatagtt tgcgcaacgt tgttgccatt    5700
gctgcaggca tcgtggtgtc acgctcgtcg tttggtatgg cttcattcag ctccggttcc    5760
caacgatcaa ggcgagttac atgatccccc atgttgtgca aaaaagcggt tagctccttc    5820
ggtcctccga tcgttgtcag aagtaagttg gccgcagtgt tatcactcat ggttatggca    5880
gcactgcata attctcttac tgtcatgcca tccgtaagat gcttttctgt gactggtgag    5940
tactcaacca agtcattctg agaatagtgt atgcggcgac cgagttgctc ttgcccggcg    6000
```

| | | | | | |
|---|---|---|---|---|---|
| tcaacacggg | ataataccgc | gccacatagc | agaactttaa | aagtgctcat | cattggaaaa 6060 |
| cgttcttcgg | ggcgaaaact | ctcaaggatc | ttaccgctgt | tgagatccag | ttcgatgtaa 6120 |
| cccactcgtg | cacccaactg | atcttcagca | tcttttactt | tcaccagcgt | ttctgggtga 6180 |
| gcaaaaacag | gaaggcaaaa | tgccgcaaaa | aagggaataa | gggcgacacg | gaaatgttga 6240 |
| atactcatac | tcttcctttt | tcaatattat | tgaagcattt | atcagggtta | ttgtctcatg 6300 |
| agcggataca | tatttgaatg | tatttagaaa | aataaacaaa | taggggttcc | gcgcacattt 6360 |
| ccccgaaaag | tgccacctga | cgtctaagaa | accattatta | tcatgacatt | aacctataaa 6420 |
| aataggcgta | tcacgaggcc | ctttcgtctt | caagaa | | 6456 |